United States Patent
Kariya et al.

(10) Patent No.: US 6,492,503 B1
(45) Date of Patent: Dec. 10, 2002

(54) GLYCOSAMINOGLYCAN AND DRUG COMPOSITIONS CONTAINING THE SAME

(75) Inventors: Yutaka Kariya, Yokohama (JP); Ryo Takano, Kyoto (JP); Kaeko Kamei, Kyoto (JP); Saburo Hara, Takatsuki (JP); Junichi Onaya, Higashimurayama (JP); Yusuke Hori, Tokyo (JP)

(73) Assignee: Seikagaku Corporation, Tokyo (JP)

( * ) Notice: Subject to any disclaimer, the term of this patent is extended or adjusted under 35 U.S.C. 154(b) by 0 days.

(21) Appl. No.: 09/509,478

(22) PCT Filed: Aug. 2, 1999

(86) PCT No.: PCT/JP99/04155

§ 371 (c)(1), (2), (4) Date: May 22, 2000

(87) PCT Pub. No.: WO00/06608

PCT Pub. Date: Feb. 10, 2000

(30) Foreign Application Priority Data

Jul. 31, 1998 (JP) ............................................. 10-217051
Aug. 31, 1998 (JP) ........................................... 10-246387

(51) Int. Cl.[7] .......................... C07H 1/00; C07H 19/00; G01N 33/00

(52) U.S. Cl. ......................... 536/1.11; 536/22.1; 436/94

(58) Field of Search .............................. 536/1.11, 22.1; 436/94

(56) References Cited

FOREIGN PATENT DOCUMENTS

| EP | 0 769 502 A | 4/1997 |
|---|---|---|
| WO | WO 95/30424 | 11/1995 |

OTHER PUBLICATIONS

Takano, R, et al. Specific 6–0–Desulfation of heparin, Carbohydrate letters, Harwood Academic Publishers, vol. 3, No. 1, 1998 pp71–77.

*Primary Examiner*—Jezia Riley
(74) *Attorney, Agent, or Firm*—Knobbe, Martens, Olson & Bear, LLP

(57) ABSTRACT

There is provided a glycosaminoglycan having a backbone structure comprising a repetitive disaccharide bearing a uronic acid residue and a glucosamine residue, and having sulfate groups, wherein substantially no sulfate group bound to the hydroxyl group at the 6-position of the glucosamine residue in the backbone structure is detected as determined by a chemical disaccharide analysis method in which the glycosaminoglycan is decomposed with nitrous acid, reacted with para-nitrophenylhydrazine and analyzed by high performance liquid chromatography, and the molar % of a uronic acid residue having a sulfate group at the 2-position is not less than 45% relative to total uronic acid residues, which is calculated from a disaccharide composition obtained by an enzymatic disaccharide analysis method in which the glycosaminoglycan is digested with glycosaminoglycan-degrading enzymes and analyzed by high performance liquid chromatography. The glycosaminoglycan can be used as an active ingredient of pharmaceuticals.

10 Claims, 8 Drawing Sheets

GLYCOSAMINOGLYCAN AND DRUG COMPOSITIONS CONTAINING THE SAME

TECHNICAL FIELD

The present invention relates to a glycosaminoglycan having sulfate groups, in which substantially all the sulfate groups bound to the 6-positions of the glucosamine residues constituting the glycosaminoglycan are removed and the removal of other sulfate groups is minimized, and to pharmaceuticals comprising the glycosaminoglycan as an active ingredient, in addition to a method for producing the glycosaminoglycan.

BACKGROUND ART

Heparin is one of glycosaminoglycans having as a backbone structure being composed of a repetitive structure of a disaccharide unit composed of a uronic acid (iduronic acid (IdoA) or glucuronic acid (GlcA)) residue and a glucosamine (GlcN) residue. Heparin is one of glycosaminoglycans in which the hydroxyl group at the 2-position of the uronic acid residue and the hydroxyl group at the 6-position and the amino group at the 2-position of the glucosamine residue each undergo a certain degree of sulfation. Because heparin has an antithorombin III (hereinafter also referred to as "ATIII") binding site (FEBS Lett. (1980) 117, 203–206), and binds with ATIII to inhibit the action of the thorombin, thereby giving rise to anticoagulative action, heparin has long been extensively used as a pharmaceutical agent such as anticoagulants for improving the results of dialysis treatment and the like. More recently, it has been found that heparin interacts with various physiological active factors. For example, heparin interacts with lipoprotein lipase (J. Biol. Chem. (1981) 256, 12893–12898) and has an affinity for basic fibroblast growth factor (J. Cell Biol. (1990) 111, 1651–1659).

Under such a situation, attention has been focusing on the domain structures within heparin that take part in the binding between heparin and specific cell growth factors or cytokines. Moreover, considerable research is being conducted relating to chemical modifications represented by desulfation of heparin aiming at reducing the anticoagulative action due to the presence of the ATIII binding site to thereby increase the interaction with physiological active factors (J. Carbohydr. Chem. (1993) 12, 507–521; Carbohydr. Res. (1989) 193, 165–172; Carbohydr. Res. (1976) 46, 87–95; WO 95/30424, etc.).

With respect to the aforementioned desulfation of heparin, in recent years the focus has been on removing the sulfate group bound to the hydroxyl group at the 6-position of the glucosamine residue in the heparin (6-desulfation). As desulfation methods, there can be mentioned the method using solvolysis (WO 95/30424) and the method using a silylating reagent (WO 96/01278).

With the former method, along with the removal of the sulfate group bound to the hydroxyl group at the 6-position of the glucosamine residue in the heparin molecule (6-O-sulfate group), the sulfate group bound to the hydroxyl group at the 2-position of the uronic acid residue (2-O-sulfate group) and the sulfate group bound to the amino group at the 2-position of the glucosamine residue (N-sulfate group) are also removed. Thus, in the course of using the former method to remove substantially all of the 6-O-sulfate groups, almost all of the N-sulfate groups of the glucosamine residues and 2-O-sulfate groups of the uronic acid residues are also lost. While the amino group at the 2-position of the glucosamine residue of the heparin thus modified can be resulfated, resulfation of the 2-position of the uronic acid residue without sulfating the 6-position of the glucosamine residue is difficult.

The latter method is superior to the former method in that it enables a more specific removal of the 6-O-sulfate group of the glucosamine residue. However, with the modified heparin thus obtained with the latter method, the effective disaccharide yield as determined by the enzymatic disaccharide analysis method is low, which means that there is still a problem with the method in that the structural identification therefor may not be enough for pharmaceutical applications. Moreover, while the anticoagulative action of the modified heparin is greatly reduced, it is not absent, and it has not been possible to obtain modified heparin in which the anticoagulative activity has been completely eliminated.

Because heparin or fragments thereof have affinities for various physiological active substances and the affinities are closely related to the functions of such substances, intensive studies have been made for search and development of drugs utilizing heparin or modified heparin. However, despite such efforts, they have yet been used effectively only as a blood anticoagulation agent in pharmaceutical applications.

That is, in focusing on using heparin for applications other than as an anticoagulant, it is important to substantially eliminate its anticoagulation and hemorrhagic actions and, with respect to using it as a pharmaceutical substance, it has to enable its "structural identification as a substance". With respect to these problems, there must be further improvements, and it has been desired to resolve these remaining problems and utilize heparin's affinities for physiologically active substances to provide drugs that are safe and useful.

DISCLOSURE OF THE INVENTION

As a result of assiduous studies aiming at resolution of the above problems, the present inventors succeeded in, by using a specific method to effect desulfation of glycosaminoglycans such as heparin that have sulfate groups, preparation of a novel glycosaminoglycan in which its anticoagulative and hemorrhagic activities were substantially eliminated while its biologically advantageous effects for living bodies such as its affinities for physiologically active substances were maintained, and unidentifiable structures were markedly reduced to the extent that the "structural identification of the substance" can be readily attained, which is important in terms of pharmaceutical applications. Thus, the present invention has been accomplished.

Specifically, it was confirmed that a glycosaminoglycan obtained by subjecting a glycosaminoglycan having sulfate groups to heat treatment at 100° C. or higher in pyridine in the presence of a silylating agent, N-methyl-N-(trimethylsilyl)-trifluoroacetamide (hereinafter also referred to as "MTSTFA") to remove substantially all of the 6-O-sulfate groups from the glucosamine residues, then evaporating the pyridine from the reaction mixture, adding water and concentrating under reduced pressure, was highly effective in promoting the healing of skin wounds and treating diabetic skin ulcers, and had fructose-1,6-bis-phosphate aldolase inhibitory activity, and that its anticoagulative and hemorrhagic activities had disappeared.

Further, it was confirmed to be possible to readily specify the structure of the glycosaminoglycan prepared by the above method with precision by using an enzymatic disaccharide analysis method utilizing glycosaminoglycan-degrading enzymes, because of the good digestibility of the glycosaminoglycan with glycosaminoglycan-degrading enzymes. This is in contrast to the previous difficulty in identifying structures of modified heparins that had been modified by being subjected to various types of chemical treatment. Using the glycosaminoglycan of which structure can thus be identified as pharmaceuticals makes it possible to provide pharmaceuticals that are highly safe and useful.

The present inventors further found that the glycosaminoglycan had high affinity for fructose-1,6-bis-phosphate aldolase, a key enzyme in the glycolytic pathway, and could be used as a strong inhibitor of that enzyme. Thus, it has become possible to provide a novel fructose-1,6-bis-phosphate aldolase inhibitor.

That is, the present invention provides the followings.

1. A glycosaminoglycan having a backbone structure comprising a repetitive disaccharide bearing a uronic acid residue and a glucosamine residue, and having sulfate groups, wherein substantially no sulfate group bound to the hydroxyl group at the 6-position of the glucosamine residue in the backbone structure is detected as determined by a chemical disaccharide analysis method in which the glycosaminoglycan is decomposed with nitrous acid, reacted with para-nitrophenylhydrazine and analyzed by high performance liquid chromatography, and the molar % of a uronic acid residue having a sulfate group at the 2-position is not less than 45%, relative to total uronic acid residues, the molar % being calculated from a disaccharide composition obtained by an enzymatic disaccharide analysis method in which the glycosaminoglycan is digested with glycosaminoglycan-degrading enzymes and analyzed by high performance liquid chromatography.

2. A glycosaminoglycan having a backbone structure comprising a repetitive disaccharide bearing a uronic acid residue and a glucosamine residue, and having sulfate groups, wherein, in a disaccharide composition of the glycosaminoglycan obtained by an enzymatic disaccharide analysis in which the glycosaminoglycan is digested with glycosaminoglycan-degrading enzymes and analyzed by high performance liquid chromatography, the total of 2-acetamido-2-deoxy-4-O-(4-deoxy-α-L-threo-hex-4-enopyranosyluronic acid)-6-O-sulfo-D-glucose, 2-deoxy-2-sulfamino-4-O-(4-deoxy-α-L-threo-hex-4-enopyranosyluronic acid)-6-O-sulfo-D-glucose, 2-acetamido-2-deoxy-4-O-(4-deoxy-2-O-sulfo-α-L-threo-hex-4-enopyranosyluronic acid)-6-O-sulfo-D-glucose and 2-deoxy-2-sulfamino-4-O-(4-deoxy-2-O-sulfo-α-L-threo-hex-4-enopyranosyluronic acid)-6-O-sulfo-D-glucose is not more than 10 mol %, and 2-deoxy-2-sulfamino-4-O-(4-deoxy-2-O-sulfo-α-L-threo-hex-4-enopyranosyluronic acid)-6-O-sulfo-D-glucose is not more than 1.5 mol %, and an effective disaccharide yield is not less than 60%.

3. The glycosaminoglycan according to the item 2, wherein, in the disaccharide composition obtained by the enzymatic disaccharide analysis method, the total of 2-acetamido-2-deoxy-4-O-(4-deoxy-2-O-sulfo-α-L-threo-hex-4-enopyranosyluronic acid)-D-glucose, 2-deoxy-2-sulfamino-4-O-(4-deoxy-2-O-sulfo-α-L-threo-hex-4-enopyranosyluronic acid)-D-glucose, 2-acetamido-2-deoxy-4-O-(4-deoxy-2-O-sulfo-α-L-threo-hex-4-enopyranosyluronic acid)-6-O-sulfo-D-glucose and 2-deoxy-2-sulfamino-4-O-(4-deoxy-2-O-sulfo-α-L-threo-hex-4-enopyranosyluronic acid)-6-O-sulfo-D-glucose is not less than 45 mol %.

4. The glycosaminoglycan according to any one of the items 1 to 3, wherein, in $^{13}C$-nuclear magnetic resonance spectrometry analysis of the glycosaminoglycan using a 5% solution of the glycosaminoglycan in deuterium oxide and sodium 3-(trimethylsilyl)propionate as a standard, substantially no peak is detected at 66.5 to 67.5 ppm and signal intensities around 100 ppm and 102 ppm are higher than signal intensity around 98.3 ppm.

5. A fructose-1,6-bis-phosphate aldolase inhibitor which comprises the glycosaminoglycan as defined in any one of the items 1 to 4 (hereinafter also referred to as "the glycosaminoglycan of the present invention") as an active ingredient.

6. A pharmaceutical composition comprising the glycosaminoglycan of the present invention as an active ingredient.

7. The pharmaceutical composition according to the item 6, which is an agent for treatment of tissue wounds and ulcers.

8. The pharmaceutical composition according to the item 6, which is an agent for treating skin diseases.

9. The pharmaceutical composition according to the item 8, wherein the agent for treating skin diseases is an agent for promoting healing of skin wounds or an agent for treating skin ulcers.

10. A method for producing the glycosaminoglycan of the present invention, comprising the following steps of:
    (a) heating a pyridine-soluble salt of glycosaminoglycan having a backbone structure comprising a repetitive disaccharide bearing a uronic acid residue and a glucosamine residue, and having sulfate groups, in pyridine at a temperature not less than 100° C. in the presence of MTSTFA for a period of time that is long enough such that substantially no sulfate group bound to the hydroxyl group at the 6-position of the glucosamine residue should be detected as determined by a chemical disaccharide analysis method in which the glycosaminoglycan is decomposed with nitrous acid, reacted with para-nitrophenylhydrazine and analyzed by high performance liquid chromatography,
    (b) evaporating the pyridine from the reaction mixture obtained in the step (a), and
    (c) adding water to the reaction mixture obtained in the step (b) and then placing the mixture under reduced pressure at an ordinary temperature.

Embodiments of the present invention will now be described.

In the present invention, the "glycosaminoglycan having a backbone structure comprising a repetitive disaccharide bearing a uronic acid residue and a glucosamine residue, and having sulfate groups" is a glycosaminoglycan having sulfate groups among the glycosaminoglycans having a heparin structure of a repetitive structure of a uronic acid residue and a glucosamine residue, and includes heparin, heparan sulfate and sulfated hyaluronic acid. The "glucosamine residue" also include those having an acetylated amino group and a sulfated amino group.

1. Glycosaminoglycan of the Present Invention

In accordance with one aspect of the present invention, there is provided a glycosaminoglycan having a backbone structure comprising a repetitive disaccharide bearing a uronic acid residue and a glucosamine residue, and having sulfate groups, wherein substantially no sulfate group bound to the hydroxyl group at the 6-position of the glucosamine residue in the backbone structure is detected as determined by a chemical disaccharide analysis method in which the glycosaminoglycan is decomposed with nitrous acid, reacted with para-nitrophenylhydrazine (also referred to as PNP-hydrazine) and analyzed by high performance liquid chromatography (hereinafter also abbreviated to as "HPLC"), and the molar % of a uronic acid residue having a sulfate group at the 2-position is not less than 45% relative to the total uronic acid residues, the molar % being calculated from a disaccharide composition obtained by an enzymatic disaccharide analysis method in which the glycosaminoglycan is digested with glycosaminoglycan-degrading enzymes and analyzed by high performance liquid chromatography. The glycosaminoglycan more preferably has an effective disaccharide yield of not less than 60% as described below.

As described later with reference to Test Method 1, the chemical disaccharide analysis method mentioned above refers to a method comprising decomposing, with nitrous acid, the material to be measured, reacting the product with para-nitrophenylhydrazine and analyzing the product by HPLC.

The description that substantially no sulfate group bound to the hydroxyl group at the 6-position of the glucosamine residue is detected, usually means that, in the aforementioned chemical disaccharide analysis method, it is not possible to detect a peak for ISMS (IdoA(2S)α1→4AnMan (6S)-PNP where AnMan(6S)-PNP denotes AnMan(6S)—CH=N—NH—PNP and AnMan(6S) denotes 2,5-anhydromannose-6-O-sulfate) produced by the above chemical treatment by the ordinary HPLC. Specifically, it can be determined by using as an index, a percentage of number of all the glucosamine residues not having a 6-O-sulfate group relative to the total glucosamine residue number in the glycosaminoglycan of the present invention that is calculated from an area of the ISM (IdoA(2S)α1→4AnMan-PNP where AnMan-PNP denotes AnMan—CH=N—NH—PNP and AnMan denotes 2,5-anhydromannose) peak and an area of the ISMS peak. For example, not less than 95% can be considered to signify "substantially not detected," and 100% to be the most preferred. For reduction of the anticoagulative action, it is preferable that there is substantially no glucosamine residue with the 6-O-sulfate group in the structure of the glycosaminoglycan of the invention. For convenience, hereinbelow the ratio of desulfation at the 6-position of the glucosamine residue will be referred to as the "6-desulfation ratio."

The 6-desulfation ratio can also be calculated from signal intensity obtained in the nuclear magnetic resonance spectrometry as described in the examples. Results obtained in this way are substantially in agreement with the "6-desulfation ratio" obtained by the aforementioned chemical disaccharide analysis method.

The position and the quantity of sulfate groups bound to the constituent sugar residues in the heparin structure of the glycosaminoglycan of the present invention can be calculated from a composition (disaccharide composition) of unsaturated disaccharides detected by an enzymatic disaccharide analysis method in which the glycosaminoglycan is digested with glycosaminoglycan-degrading enzymes and analyzed by high performance liquid chromatography (enzymatic disaccharide analysis method utilizing a combination of digestion with glycosaminoglycan-degrading enzymes and HPLC).

The "molar % of a uronic acid residue having a sulfate group at the 2-position relative to total uronic acid residues" means, taking as 100% the total amount of the unsaturated disaccharides expressed by the general formula mentioned below [total (molar number) of 2-acetamido-2-deoxy-4-O-(4-deoxy-α-L-threo-hex-4-enopyranosyluronic acid)-D-glucose (hereinafter referred to as "ΔDiHS-OS"), 2-deoxy-2-sulfamino-4-O-(4-deoxy-α-L-threo-hex-4-enopyranosyluronic acid)-D-glucose (hereinafter referred to as "ΔDiHS-NS"), 2-acetamido-2-deoxy-4-O-(4-deoxy-α-L-threo-hex-4-enopyranosyluronic acid)-6-O-sulfo-D-glucose (hereinafter referred to as "ΔDiHS-6S"), 2-acetamido-2-deoxy-4-O-(4-deoxy-2-O-sulfo-α-L-threo-hex-4-enopyranosyluronic acid)-D-glucose (hereinafter referred to as "ΔDiHS-US"), 2-deoxy-2-sulfamino-4-O-(4-deoxy-α-L-threo-hex-4-enopyranosyluronic acid)-6-O-sulfo-D-glucose (hereinafter referred to as "ΔDiHS-di(6,N)S"), 2-deoxy-2-sulfamino-4-O-(4-deoxy-2-O-sulfo-α-L-threo-hex-4-enopyranosyluronic acid)-D-glucose (hereinafter referred to as "ΔDiHS-di(U,N)S"), 2-acetamido-2-deoxy-4-O-(4-deoxy-2-O-sulfo-α-L-threo-hex-4-enopyranosyluronic acid)-6-O-sulfo-D-glucose (hereinafter referred to as "ΔDiHS-di(U,6)S"), and 2-deoxy-2-sulfamino-4-O-(4-deoxy-2-O-sulfo-α-L-threo-hex-4-enopyranosyluronic acid)-6-O-sulfo-D-glucose (hereinafter referred to as "ΔDiHS-tri(U,6,N)S"], a ratio of the aforementioned unsaturated disaccharides each having the sulfate group at the 2-position of the uronic acid residue (total (molar number) of ΔDiHS-US, ΔDiHS-di(U,N)S, ΔDiHS-di(U,6)S, and ΔDiHS-tri(U,6,N)S) represented in terms of percentage as determined in the analysis by the enzymatic disaccharide analysis method utilizing the combination of digestion with glycosaminoglycan-degrading enzymes and HPLC. To maintain the high activity for treatment of skin diseases of the glycosaminoglycan of the present invention, this value is usually not less than 45%, preferably not less than 50%, and more preferably not less than 60%. The disaccharide analysis method utilizing the combination of enzymatic digestion and HPLC refers to the enzymatic disaccharide analysis method utilizing a combination of enzymatic digestion and HPLC described in Test Method 2 later.

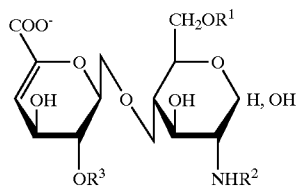

TABLE 1

| Unsaturated | Substituents in structural formula | | |
|---|---|---|---|
| disaccharide | $R^1$ | $R^2$ | $R^3$ |
| ΔDiHS-OS | H | $COCH_3$ | H |
| ΔDiHS-NS | H | $SO_3^-$ | H |
| ΔDiHS-6S | $SO_3^-$ | $COCH_3$ | H |
| ΔDiHS-US | H | $COCH_3$ | $SO_3^-$ |
| ΔDiHS-di(6,N)S | $SO_3$ | $SO_3$ | H |
| ΔDiHS-di(U,N)S | H | $SO_3^-$ | $SO_3^-$ |
| ΔDiHS-di(U,6)S | $SO_3^-$ | $COCH_3$ | $SO_3^-$ |
| ΔDiHS-tri(U,6,N)S | $SO_3^-$ | $SO_3^-$ | $SO_3^-$ |

The structures denoted by the above abbreviations can also be represented as shown below: ΔDiHS-OS: ΔHexA1→4GlcNAc; ΔDiHS-NS: ΔHexA1→4GlcNS; ΔDiHS-6S: ΔHexA1→4GlcNAc(6S); ΔDiHS-US: ΔHexA (2S)1→4GlcNAc; ΔDiHS-di(6,N)S: ΔHexA1→4GlcNS (6S); ΔDiHS-di(U,N)S: ΔHexA(2S)1→4GlcNS; ΔDiHS-di (U,6)S: ΔHexA(2S)1→4GlcNAc(6S); ΔDiHS-tri(U,6,N)S: ΔHexA(2S)1→4GlcNS(6S).

In the above formulas, ΔHexA represents unsaturated hexuronic acid, GlcNAc represents N-acetylglucosamine, GlcNS represents N-sulfated glucosamine, and binding positions of sulfate groups are shown in the parentheses.

The numerical values obtained by the enzymatic disaccharide analysis method reflect the position and number of sulfate groups of the glycosaminoglycan prior to enzymatic digestion. For more accurate reflection, the enzymatic digestion has to be more uniform and the digestibility (enzymatic digestibility (Test Method 4 described below)) as high as possible, usually not less than 60%, preferably not less than 70%, and more preferably not less than 80%.

Further, the effective disaccharide yield of the glycosaminoglycan that is calculated by means of the enzymatic disaccharide analysis method, and shows the proportion of disaccharide units that can be identified by the method within the glycosaminoglycan to be the object of the analysis. The effective disaccharide yield, which is an index of the ease of structure identification, is usually not less than 60%, preferably not less than 70%, and more preferably not less than 80%.

The "effective disaccharide yield" is a value expressed as a percentage, obtained by multiplying a ratio of the total area of the peaks of the identifiable unsaturated disaccharides (ΔDiHS-OS, ΔDiHS-NS, ΔDiHS-6S, ΔDiHS-US, ΔDiHS-di(6,N)S, ΔDiHS-di(U,N)S, ΔDiHS-di(U,6)S and ΔDiHS-tri(U,6,N)S) to the total area of the peaks of the unsaturated disaccharides detected by HPLC used in the aforementioned disaccharide analysis method, by an enzyme digestibility.

In the case of the glycosaminoglycan of the present invention, unsaturated disaccharides that contain a glucosamine residue having a sulfate group at the 6-position (the total of ΔDiHS-6S, ΔDiHS-di(6,N)S, ΔDiHS-di(U,6)S and ΔDiHS-tri(U,6,N)S) is not more than 10 mol %, preferably not more than 5 mol %, and ΔDiHS-tri(U,6,N)S is not more than 1.5 mol %, preferably not more than 1 mol %, and more preferably it is undetectable, as analyzed by the enzymatic disaccharide analysis method (in the disaccharide composition).

The 6-desulfation ratio of the glycosaminoglycan of the present invention calculated by using the standard heparin mentioned below as a reference is normally not less than 90%, when analyzed by the enzymatic disaccharide analysis method.

Heparin has been known to show interaction with (affinity for) various cytokines (for example, fibroblast growth factor, hepatocyte growth factor, vascular endothelial cell growth factor, transforming growth factor, epidermal growth factor, midkine, interleukin 8, vitronectin, heparin-binding brain cell mitogenic factor, and heparin-binding neurite outgrowth-promoting factor and so forth), and it has been known that sulfate groups bound to the heparin structure play a major part in such interactions. Because the glycosaminoglycan of the present invention has substantially no 6-O-sulfate group of the glucosamine residue, although the anticoagulative action, the affinity for the ATIII that plays a major part in that action, and the hemorrhagic action are lost, the heparin interaction with (affinity for) the aforementioned cytokines are maintained. In the glycosaminoglycan of the invention, therefore, to maintain the affinity, the molar % of the unsaturated disaccharides having glucosamine residues with a sulfate group bound to the amino group at the 2-position (the total of ΔDiHS-NS, ΔDiHS-di(6,N)S, ΔDiHS-di(U,N)S and ΔDiHS-tri(U,6,N)S) is preferably not less than 65 mol %, more preferably not less than 75 mol %, in the composition (disaccharide composition) of unsaturated disaccharides as obtained by using the above-mentioned enzymatic disaccharide analysis method. And as described above, the molar % of the uronic acid residue having a 2-O-sulfate group relative to the total uronic acid residues is normally not less than 45%, preferably not less than 50%, most preferably not less than 60%.

Moreover, to maintain the affinity for the cytokines, when sodium 3-(trimethylsily)propionate (hereinbelow abbreviated to "TSP") is used as a reference (0 ppm) in the structural analysis by $^{13}C$-nuclear magnetic resonance (NMR) spectrometry using a deuterium oxide solution (described in Example 3 below), it is preferred that substantially no peak should be observed at 66.5 to 67.5 ppm, while a peak is observed at 70.0 to 71.0 ppm, and it is further preferred that, when the signal intensities around 98.3 ppm, 100 ppm and 102 ppm are compared, both of the signal intensities around 100 ppm and 102 ppm should be higher than the signal intensity around 98.3 ppm. In one of the most preferred embodiments of the glycosaminoglycan of the present invention, no continuous peak is observed in a region of from 96.5 to 97.0 ppm in addition to the aforementioned characteristics.

The glycosaminoglycan of the present invention preferably has high activity for promoting activities of the aforementioned cytokines, inter alila, the activity of basic fibroblast growth factor (bFGF) (cell proliferation-promoting activity), and it preferably has an activity for promoting bFGF activity corresponding to not less than 80%, more preferably not less than 90% of the bFGF activity-promoting activity of a standard heparin or a commercially available heparin as determined by the method for measuring bFGF activity-promoting activity in which the bFGF activity-promoting activity is measured for cultured cells subjected to cell proliferation inhibition by using $NaClO_3$ (see Test Method 9 in Examples, Measurement 1 for bFGF activity-promoting activity). Furthermore, the glycosaminoglycan of the present invention also preferably has an activity for promoting bFGF activity corresponding to not less than 70%, more preferably not less than 80%, most preferably not less than 90% of the bFGF activity-promoting activity of a standard heparin or a commercially available heparin as determined by the method for measuring bFGF activity-promoting activity in which the bFGF activity-promoting activity is measured for cultured cells cultured without using $NaClO_3$ (see Test Method 9 in Examples, Measurement 2 for bFGF activity-promoting activity).

Because the highly-sulfated region (sulfated cluster) in the backbone structure of heparin strongly concerning the anticoagulative activity and the hemorrhagic activity is detected as ΔDiHS-tri(U,6,N)S by the aforementioned disaccharide analysis method, in the glycosaminoglycan of the present invention, ΔDiHS-tri(U,6,N)S is not more than 1.5 mol %, preferably not more than 1 mol %, most preferably it is undetectable, in the composition (disaccharide composition) of unsaturated disaccharides as determined by the aforementioned enzymatic disaccharide analysis method. Such glycosaminoglycan of the present invention has substantially lost the anticoagulative activity and the hemorrhagic activity.

The glycosaminoglycan of the present invention preferably has an average molecular weight of 3,000–30,000 more preferably 5,000–20,000, most preferably 7,000–16,000 as determined by using gel filtration, but it is not particularly limited.

As mentioned above, the glycosaminoglycan of the present invention has substantially lost the anticoagulative activity and the hemorrhagic activity. That is, when the activated partial thromboplastin time (also abbreviated as "APTT" hereinafter) and the thromboplastin time (also abbreviated as "TT" hereinafter) are measured with addition of the glycosaminoglycan of the present invention at a final concentration of 30 μg/ml in a reaction mixture in the measurement methods of APTT and TT (Test Methods 5 and 6), APTT does not exceed 50 seconds, and with addition at a final concentration of 100 μg/ml, TT does not exceed 50 seconds.

Furthermore, in the measurement of antithrombin activity using bovine ATIII (for example, the method described in [Measurement method for antithrombin activity] in the Test Method mentioned below (Test Method 7) and so forth), a concentration affording 50% inhibition ($IC_{50}$) is preferably not less than 50 μg/ml, more preferably not less than 100 μg/ml.

Because the glycosaminoglycan of the present invention has substantially lost the anticoagulative activity and the hemorrhagic activity as mentioned above, and has excellent wound healing-promoting activity and skin ulcer treatment activity as will be demonstrated in the examples mentioned below, it is useful as an active ingredient of pharmaceuticals.

While the glycosaminoglycan of the present invention can also be used in a free form, it is preferably obtained as a pharmaceutically acceptable salt. Examples of such a salt include, for example, those pharmaceutically acceptable salts selected from alkali metal salts such as sodium salts and potassium salts, alkaline earth metal salts such as magnesium salts and calcium salts, ammonium salts, amine salts such as tributylamine salts and so forth, but alkali metal salts, in particular, sodium salts are preferred.

2. Inhibitor of the Present Invention

The inhibitor of the present invention is a fructose-1,6-bisphosphate aldolase inhibitor characterized by containing the glycosaminoglycan of the present invention as an active ingredient.

The aforementioned glycosaminoglycan of the present invention which can be used as an active ingredient of the inhibitor of the present invention exhibits high affinity for fructose-1,6-bisphosphate aldolase (abbreviated as "FPA" hereinafter) known as an enzyme which controls reaction rates of glycolysis enzymes, and has an activity for inhibiting the reaction of the enzyme. Therefore, the glycosaminoglycan of the present invention can inhibit the whole glycolysis pathway, and hence it can be used as an active ingredient of a glycolysis inhibitor, in particular, an FPA inhibitor.

As demonstrated in the examples mentioned below, it was found that any of (1) the glycosaminoglycan of the present invention, (2) a derivative corresponding to heparin from which only the sulfate group bound to the hydroxyl group at the 2-position of the uronic acid residue of heparin through the ester bond is removed (2ODSH), and (3) a derivative corresponding to heparin from which only the sulfate group bound to the amino group to the 2-position of the glucosamine residue of heparin through the amide bond is removed (NDSH) showed affinity for FPA and inhibits the activity of FPA. While these results indicated that heparin showed the highest activity for inhibiting FPA, it was also found that, among the substances of (1), (2) and (3), the glycosaminoglycan of the present invention showed the highest FPA inhibitory activity, the derivative of (2) showed secondly high inhibitory activity, and the derivative of (3) showed the weakest inhibitory activity. Therefore, those experimental results indicate that it is most important to have the sulfate group at the amino group at the 2-position of the glucosamine residue in the heparin structure, it is secondary important to have the sulfate group bound to the hydroxyl group at the 2-position of the uronic acid residue in the heparin structure for the FPA activity, and the sulfate group of the least involvement is the sulfate group bound to the hydroxyl group at the 6-position of the glucosamine residue through the ester bond. The present invention was accomplished based on these findings, and the inhibitor of the present invention is an FPA inhibitor containing, as an active ingredient, the glycosaminoglycan of the present invention having high FPA inhibitory activity comparable to that of heparin and reduced side effects shown by heparin such as hemorrhagic activity.

The glycosaminoglycan of the present invention used as an active ingredient of the FPA inhibitor preferably contains not less than 40 mol % of a glucosamine residue of which amino group at the 2-position is sulfated, relative to the total amount of glucosamine residues constituting the backbone structure of glycosaminoglycan. More specifically, in the aforementioned enzymatic disaccharide analysis method (disaccharide composition), the molar % of unsaturated disaccharides containing glucosamine residues having the sulfate group at the 2-position (ΔDiHS-NS, ΔDiHS-di(6,N)S, ΔDiHS-di(U,N)S, ΔDiHS-tri(U,6,N)S) is preferably not less than 40 mol %, more preferably not less than 50 mol %. Further, the glycosaminoglycan of the present invention used as an active ingredient of the FPA inhibitor preferably contains not less than 45 mol % of a uronic acid residue of which hydroxyl group at the 2-position is sulfated, relative to the amount of uronic acid residues constituting the backbone structure of the glycosaminoglycan. More specifically, in the aforementioned enzymatic disaccharide analysis method (disaccharide composition), the molar % of uronic acid residues having the sulfate group at the 2-position (ΔDiHS-US, ΔDiHS-di(U,6)S, ΔDiHS-di(U,N)S, ΔDiHS-tri(U,6,N)S) is normally not less than 45 mol %, preferably not less than 50 mol %.

The glycosaminoglycan of the present invention used as an active ingredient of the FPA inhibitor preferably has Ki values of less than 0.4 μg/ml and less than 2.5 μg/ml for the isozymes A4 and C4 of bovine brain fructose-1,6-bisphosphate aldolase, respectively, as determined under the conditions mentioned in Example 15 described below.

The inhibitor of the present invention can be used as agents for treatment and prevention of diseases or disorders accompanied by hypermetabolism of the glycolysis pathway. Examples of such diseases or disorders accompanied by hypermetabolism of the glycolysis pathway include, for example, infection of malaria parasite and so forth, and pharmaceutials containing the inhibitor of the present invention are considered to exhibit therapeutic or prophylactic effect for such diseases or disorders.

3. Pharmaceutical Composition of the Present Invention

The pharmaceutical composition of the present invention is characterized by containing the glycosaminoglycan of the present invention as an active ingredient.

Because the aforementioned glycosaminoglycan of the present invention is substantially free from the anticoagulative activity and the hemorrhagic activity which are considered to become problems as side effects, it can be administered to a living body as a drug.

Among the physiological activities possessed by the glycosaminoglycan of the present invention, particularly remarkable are activities for promoting tissue wound or ulcer healing, and the glycosaminoglycan of the present invention can be utilized as an agent for treatment (including prophylactic agent) of wounds and ulcers of tissues. The aforementioned tissue include epithelial tissues such as skin, cornea and mucosae including nasal cavity mucosa and oral cavity mucosa, connective tissues such as cartilage and bone and nervous tissues, as well as alimentary tract and blood vessel tissues and so forth. The wound includes disorders occurring in the aforementioned tissues (e.g., injury caused by an external force, wound of burn etc.). Among those, a preferred embodiments of the pharmaceutical composition of the present invention is, in particular, an agent for promoting healing of wounds or ulcers produced on skin (agent for treatment of skin diseases), and the most preferred embodiments of the pharmaceutical composition of the present invention are an agent for promoting healing of skin wounds and an agent for treatment of skin ulcers. The aforementioned skin ulcer include, for example, in addition to usual ulcers, intractable skin ulcers such as lower extremity ulcer and decubital ulcer (diabetic skin ulcer is also included).

Because the glycosaminoglycan of the present invention exhibits high affinity for bFGF and high activity for promoting its activity as demonstrated in the examples described below, the pharmaceutical composition of the present invention can also be utilized in embodiments intended to be applied to disorders and diseases healing of which is considered to involve bFGF, in addition to the aforementioned embodiments, and it exhibits more excellent effect compared with pharmaceuticals containing known modified heparins. Examples of such disorders and diseases include, for example, periodontal disease, restenosis, cancer, diseases involving neovascularization (proliferating retinitis, rheumatoid arthritis, psoriasis etc.), ischemic reperfusion disorder, inflammation, various circulatory organ diseases and so forth.

Moreover, as explained for the inhibitor of the present invention, because the glycosaminoglycan of the present invention has FPA inhibitory activity, it can be utilized as an agent for treatment and prevention of diseases accompanied by hypermetabolism of the glycolysis pathway.

Therefore, skin diseases can be treated and diseases accompanied by hypermetabolism of the glycolysis pathway can be treated or prevented by administering an effective amount of the glycosaminoglycan of the present invention to a subject in need of treatment of skin diseases or treatment or prevention of diseases accompanied by hypermetabolism of the glycolysis pathway.

Dosage forms and administration routes used when the pharmaceutical composition of the present invention is administered to a living body can be suitably selected depending on characteristics and severity of diseases of interest. For example, the glycosaminoglycan of the present invention can safely be administered parenterally or orally as it is, or in the form of a pharmaceutical composition containing other pharmaceutically acceptable carriers, excipients, diluents and so forth (for example, external preparations such as solutions, suspensions, ointments, plasters, lotions, pastes, liniments and patches, and injections, suppositories, tablets, capsules and so forth) to warm blooded animals (for example, human, mouse, rat, hamster, rabbit, dog, cat, horse and so forth).

When the glycosaminoglycan of the present invention is utilized as an agent for treatment of skin diseases, parenteral administration is particularly preferred, and dosage forms suitable for such administration include the aforementioned external preparations. Administration can be attained by, but not limited to, dropping, application, plastering and so forth.

Formulating amounts in the compositions and administration amounts of the glycosaminoglycan of the present invention should be individually decided depending on administration schemes of the preparations, dosage forms, specific conditions of patients, body weight of patients and so forth, and they are not particularly limited. However, the administration amount of the glycosaminoglycan of the present invention is generally, for example, about 100 μg/kg to about 100 mg/kg a day. As for administration frequency of the preparations, it may be one time a day, or it may be 2–4 times or more a day.

The amount of the glycosaminoglycan of the present invention to be added to the pharmaceutical composition of the present invention varies depending on the dosage form of the composition. It may be, for example, about 10 μg to 50 mg per unit of the composition, but it should be suitably controlled depending on the dosage form, specific conditions of patients and so forth.

The 50% lethal dose ($LD_{50}$) of normal heparin determined by an acute toxicity test in mice (male and female) has been known to be not less than 5,000 mg/kg for oral administration, not less than 2,500 mg/kg for subcutaneous or intraperitoneal administration, or not less than 1,000 mg/kg for intravenous injection, and it is generally used as a drug (anticoagulant) at present. Therefore, its safety has already been established.

On the other hand, the glycosaminoglycan of the present invention used for the pharmaceutical composition of the present invention showed no death when it was administered to normal rats and mice with hereditary diabetes as indicated in the examples mentioned below. Further, the glycosaminoglycan of the present invention is a substance produced based on heparin, and shows extremely reduced anticoagulative activity and hemorrhagic activity as compared with heparin or has substantially lost these activities. Therefore, the pharmaceutical composition of the present invention containing the glycosaminoglycan of the present invention can be said to be highly safe for warm blooded animals.

4. Production Method of the Present Invention

The production method of the present invention is a method for producing the aforementioned glycosaminoglycan of the present invention, and includes the following steps:

(a) heating a pyridine-soluble salt of glycosaminoglycan having a backbone structure comprising a repetitive disaccharide bearing a uronic acid residue and a glucosamine residue, and having sulfate groups, in pyridine at a temperature not less than 100° C. in the presence of MTSTFA for a period of time that is long enough such that substantially no sulfate group bound to the hydroxyl group at the 6-position of the glucosamine residue should be detected as determined by the enzymatic disaccharide analysis method, (b) evaporating the pyridine from the reaction mixture obtained in the step (a), and (c) adding water to the reaction mixture obtained in the step (b) and then placing the mixture under reduced pressure at an ordinary temperature.

An example of the production method of the present invention will be explained below.

(a) Step of Heating a Pyridine-soluble Salt of Heparin in Pyridine at a Temperature not Less than 100° C. in the Presence of MTSTFA The "pyridine-soluble salt of glycosaminoglycan having a backbone structure comprising a repetitive disaccharide bearing a uronic acid residue and a glucosamine residue, and having sulfate groups" used in the production method of the present invention is preferably a pyridinium salt of heparin, while it is not particularly limited so long as it is a pyridine-soluble salt of heparin. Such a pyridinium salt of heparin can be obtained by, for example, passing sodium salt of heparin thorough a cation exchange column (for example, a column packed with Amberlite IR-120B ($H^+$ form) resin (produced by ORGANO CORP.)) which is equilibrated with distilled water to be converted into a free form, and adding excessive pyridine to the resulted acidic fraction to adjust pH thereof to 5 to 7, preferably 5.5 to 6.5, and lyophilizing the fraction. A commercially available heparin pyridinium salt may also be used.

The aforementioned pyridine-soluble salt of heparin is reacted in pyridine in the presence of MTSTFA. The MTSTFA used for the reaction is added in an amount of normally 6- to 12-fold volume (w/w), preferably 8- to 11-fold volume (w/w) of the pyridine-soluble salt of heparin. The amount of pyridine used for the reaction is preferably 5- to 150-fold volume (v/w), preferably 10- to 120-fold volume (v/w), most preferably 15- to 110-fold volume (v/w) of the pyridine-soluble salt of heparin, but it is not limited to these amounts.

Temperature for the aforementioned reaction is preferably 100–115° C., most preferably 108–112° C. The period of time that is long enough such that substantially no sulfate group bound to the hydroxyl group at the 6-position of the glucosamine residue should be detected in the chemical disaccharide analysis method is, when a temperature within the aforementioned preferred temperature range is maintained, preferably 90 to 150 minutes, most preferably 100 to 130 minutes. Moreover, by maintaining the aforementioned temperature for 10–20 minutes, 25–35 minutes, or 50–70 minutes, for example, it is also possible to prepare a glycosaminoglycan having about 50%, about 70%, or about 90% of 6-desulfation ratio, respectively. That is, in the production method of the present invention, it is possible to precisely control the 6-desulfation ratio by controlling the reaction time as described above.

After the completion of the aforementioned reaction, the reaction is preferably stopped by cooling the reaction mixture. Such cooling can be attained by, for example, leaving a vessel containing the reaction mixture at room temperature, or cooling it with flowing water or ice. While the method for cooling is not particularly limited, it is preferably attained by ice cooling.

(b) Step of Evaporating Pyridine

The pyridine is evaporated from the cooled reaction mixture. While the pyridine can be evaporated by any known method for evaporating organic solvents, it is preferably performed by using an evaporator at 25 to 37° C. under reduced pressure, because of ease of its operation. The reaction mixture is concentrated by the evaporation. As for the degree of concentration of the reaction mixture, it is preferably 7- to 25-fold concentration, most preferably 8- to 20-fold concentration of the reaction mixture.

The term "reduced pressure" usually means a pressure of $10^{-2}$ to $10^{-4}$ Torr.

(c) Step of Adding Water and Placing under Reduced Pressure at Ordinary Temperature To the reaction mixture concentrated through the evaporation of pyridine, water is added in order to decompose MTSTFA bound to hydroxyl groups and free MTSTFA. The amount of water to be added is preferably 1.5- to 3-fold amount, most preferably 1.8- to 2.5-fold amount with respect to the concentrated reaction mixture. When water is added to the concentrated reaction mixture as described above, white turbidity is produced in the reaction mixture. To eliminate the white turbidity, the concentrated reaction mixture to which water is added is placed under reduced pressure at an ordinary temperature. The reduced pressure at an ordinary temperature can be realized by using an evaporator, and the reduced pressure is preferably maintained at 25 to 37° C. until the white turbidity disappears. The reduced pressure is normally maintained for 5 to 10 minutes. The reduced pressure is preferably a pressure of $10^{-2}$ to $10^{-4}$ Torr like the aforementioned reduced pressure, and it is preferably a pressure under which the concentrated reaction mixture is boiled because of the reduced pressure.

(d) Other Steps

After the treatment of the aforementioned step (c), decomposition products of MTSTFA and the organic solvent are preferably removed from the reaction mixture. To this end, known methods can be used, which include methods utilizing dialysis, ethanol precipitation, cation exchange column and so forth.

When dialysis is used, only flowing water or a combination of flowing water and distilled water can be used for the outer liquid of the dialysis. When dialyzed against flowing water, the dialysis is normally performed for at least 24 hours, preferably at least 40 hours, most preferably 48 hours. When dialysis is performed by using a combination of flowing water and distilled water, the reaction mixture can be dialyzed against flowing water, and then dialyzed against distilled water. After the dialysis is performed against flowing water as described above, the dialysis against distilled water is normally performed for at least 1 hour, preferably 1.5 to 2.5 hours.

From the reaction mixture from which the decomposition products of MTSTFA and the organic solvent are removed, the glycosaminoglycan of the present invention can be obtained in the form of a salt thereof by a usual method for precipitating glycosaminoglycans.

As the method for obtaining the glycosaminoglycan of the present invention as a salt, there can be mentioned, for example, a method comprising fractionating the inner solution obtained from the dialysis by using a cation exchange column (for example, a column packed with Amberlite IR-120B ($H^+$ form) resin (produced by ORGANO CORP.)) equilibrated with distilled water to collect an acidic fraction, adjusting pH of the acidic fraction to 8 to 10, preferably 8.5 to 9.5 by adding an aqueous alkaline solution (for example, aqueous alkali metal hydroxide or alkaline earth metal hydroxide such as aqueous sodium hydroxide, aqueous potassium hydroxide, aqueous magnesium hydroxide, and aqueous calcium hydroxide preferably at a concentration of 0.1–2 N), dialyzing the fraction against flowing water for normally at least 15 hours, preferably about 18 hours, then against distilled water for normally 1.5 to 2.5 hours, and lyophilizing the inner solution obtained from the dialysis. By this method, a lyophilized product of the glycosaminoglycan of the present invention can be obtained.

A modified version of the glycosaminoglycan of the present invention with different degrees of sulfation at the 2-position of the glucosamine residue and the 2-position of the uronic acid residue can be prepared by changing such sulfation degrees of the glycosaminoglycan of the present invention as required by appropriately using a method comprising sulfating the amino group at the 2-position of the glucosamine residue or the hydroxyl group at the 2-position of the uronic acid residue constituting the backbone structure, and a method comprising releasing the sulfate group at the 2-position of the uronic acid residue constituting the backbone structure in combination.

As the method for sulfating the amino group at the 2-position of the glucosamine residue, for example, the method of Nagasawa et al. (Carbohydr. Res., (1989) 193, 165–172) with modification can be mentioned. That is, the glycosaminoglycan of the present invention or a salt thereof is dissolved in an alkaline solution at about pH 9 to 10 (for example, sodium carbonate solution, sodium hydroxide solution, potassium hydroxide solution etc.), and solid trimethylammonium sulfonate or triethylammonium sulfonate is additionally added at 50 to 55° C. over 6 to 24 hours.

Further, as the method for sulfating the hydroxyl group at the 2-position of the uronic acid residue, for example, there can also be mentioned the method of Nagasawa et al. (Carbohydr. Res. (1989) 193, 165–172), which is the same method as mentioned above, with modification. That is, the glycosaminoglycan of the present invention is made into a tributylammonium salt by salt exchange in a conventional manner, and the obtained tributylammonium salt of the glycosaminoglycan of the present invention is fully dissolved in N,N-dimethylformamide, and allowed to react with 5 to 20 molar equivalents/(mole of free hydroxyl groups) of sulfated pyridine at −10 to 0° C. for 1 hour. However, in this method, along with the sulfation of the hydroxyl group at the 2-position of the uronic acid residue, the sulfate group at the 6-position of the glucosamine residue are also sulfated. Therefore, when this method is used, it is preferable to subject the product to the method for producing the glycosaminoglycan of the present invention again to release the sulfate group at the 6-position of the glucosamine residue.

As the method for releasing the sulfate group at the 2-position of the uronic acid residue, there can be mentioned, for example, a partially modified version of the method of Jaseja et al. (Can. J. Chem. (1989) 67, 1449–1456). That is, a sodium salt of the glycosaminoglycan of the present invention is dissolved in a NaOH solution, and lyophilized immediately. The obtained lyophilized powder is dissolved in distilled water, and adjusted to pH 6 to 8, preferably pH 6.5 to 7.5, by addition of acetic acid. Then, this solution is subjected to dialysis and lyophilized.

A preparation of the glycosaminoglycan of the present invention preferably contains less contaminated endotoxins. In particular, the amount of such contaminated endotoxins (endotoxin activity) contained in 1 mg of a preparation of the glycosaminoglycan of the present invention is preferably, but not limited to, not more than 0.2 USP endotoxin unit (EU), more preferably not more than 0.1 EU, most preferably less than 0.05 EU.

Further, a preparation of the glycosaminoglycan of the present invention preferably has a content of residual pyridine of not more than 200 ppm, more preferably not more than 150 ppm, most preferably not more than 100 ppm, in order to secure safety when the preparation of the glycosaminoglycan of the present invention is used as a raw material of pharmaceutials. According to the Japanese Pharmacopoeia, the residual pyridine content in pharmaceutical preparations is regulated to be not more than 200 ppm.

BRIEF DESCRIPTION OF THE DRAWINGS

FIG. 1 (1) shows $^{13}$C-MNR spectrum of the standard heparin (Standard H). FIG. 1 (2), (3), (4) and (5) show $^{13}$C-MNR spectra of glycosaminoglycans obtained by changing the reaction time at 110° C. to 15, 30, 60 and 120 minutes, respectively (Control 3, Control 4, Control 5 and Invention 2). In the figure, 6S is a signal of the 6-position carbon atom of a glucosamine residue having a 6-O-sulfate group and 6 is a signal of the 6-position carbon atom of a glucosamine residue without a 6-O-sulfate group.

BEST MODE FOR CARRYING OUT THE INVENTION

Figure 1:
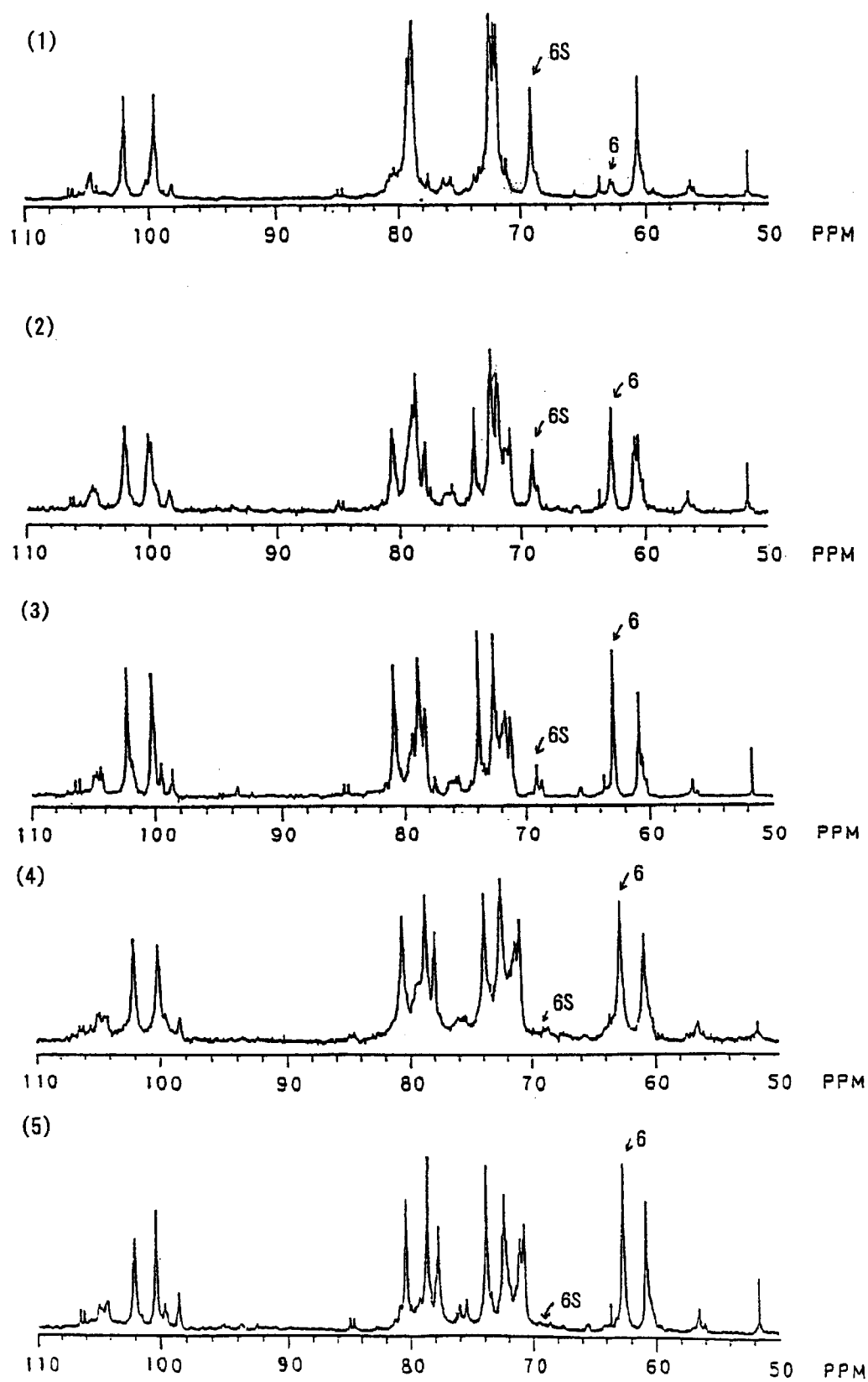
FIG. 1 shows time course of change of $^{13}$C-MNR spectrum during the preparation of a glycosaminoglycan of the present invention (Invention 2).

Hereafter, the present invention will be more specifically explained with reference to the following Examples.

First, test methods will be explained.

Test Method 1

[Detection of Sulfate Group Bound to Hydroxyl Group at 6-Position of Glucosamine Residue by Using Chemical Disaccharide Analysis Method and Calculation of 6-Desulfation Ratio]

According to the method of Kariya et al. (Kariya et al., J. Biochem. (1998) 123, 240–246), the 6-desulfation ratio of a test substance was determined. That is, 100 μl of nitrous acid solution (pH 1.5) was added to 1 mg of a sample and maintained at room temperature for 10 minutes. The mixture was adjusted to pH 7.5 with 1 N sodium carbonate, and dried by an inert gas blow onto it. To the dried product, 200 μl of distilled water and 200 μl of acetonitrile containing 1% PNP-hydrazine was added and the mixture was maintained at 37° C. for 30 minutes to allow reaction for coupling of glycosaminoglycan and PNP. Then, it was partially purified by using SepPak C-18 cartridge column (Waters). The partially purified product was analyzed by IPRP-HPLC (ion-pairing reversed-phase HPLC) to confirm the presence or absence of a peak of ISMS (IdoA(2S)-AnMan(6S)-PNP). Further, peak areas of ISM (IdoA(2S)-AnMan-PNP) and ISMS (IdoA(2S)-AnMan(6S)-PNP) were calculated and the obtained values were used to calculate the 6-desulfation ratio according to the following formula:

$$\text{6-Desulfation ratio}=(B_0 \times A_1 - A_0 \times B_1)/(B_0(A_1+B_1)) \times 100(\%)$$

wherein, $A_0$ is the peak area of ISM when the standard heparin mentioned below is used as a sample, $B_0$ is the peak area of ISMS when the standard heparin mentioned below is used as a sample, $A_1$ is the peak area of ISM when a test substance (used as a generic name for substances to be measured such as standard heparin, glycosaminoglycan of the present invention etc.) is used as a sample, and $B_1$ is the peak area of ISMS when the test substance is used as a sample.

Test Method 2

[Enzymatic Disaccharide Analysis Method Utilizing Combination of Digestion with Glycosaminoglycan-degrading Enzymes and High Performance Liquid Chromatography]

(1) Digestion with Glycosaminoglycan-degrading Enzymes 1.0 mg of a test substance was dissolved in 220 μl of 20 mM sodium acetate (pH 7.0) containing 2 mM calcium acetate. Glycosaminoglycan-degrading enzymes (20 mU each of heparinase, heparitinase I and II) were added thereto, and allowed to react at 37° C. for 2 hours.

(2) Analysis by HPLC

The enzymatic digest in the solution obtained by the above (1) (20 μl) was analyzed by using HPLC (Shimadzu Corp., Model LC6AD) under the following conditions. An ion-exchange column (Dionex, CarboPac PA-1 column, φ 4.0×250 mm) was used in accordance with a known method (Kariya, et al., Comp. Biochem. Physiol. (1992) 103B, 473–479) to perform elution at a flow rate of 1 ml per minute by using a lithium chloride gradient (50 mM→2.5 M), and absorbance at 232 nm was measured.

(3) Calculation of Disaccharide Composition, Molar % of 2-O-Sulfated Uronic Acid Residue in all Uronic Acid Residues and Effective Disaccharide Yield The disaccharide composition was obtained by determining the quantity of each identifiable unsaturated disaccharide (ΔDiHS-OS, ΔDiHS-NS, ΔDiHS-6S, ΔDiHS-US, ΔDiHS-di(6,N)S, ΔDiHS-di(U,N)S, ΔDiHS-di(U,6)S and ΔDiHS-tri(U,6,N)S) from peak areas detected by HPLC in the above (2), and calculating the proportion of each unsaturated disaccharide (molar %). The molar % of 2-O-sulfated uronic acid residue in all uronic acid residues was calculated as a proportion of the unsaturated disaccharide having the sulfate group at the 2-position of the uronic acid residue (total area of peaks of ΔDiHS-US, ΔDiHS-di(U,N)S, ΔDiHS-di(U,6)S and ΔDiHS-tri(U,6,N)S) taking the total quantity of unsaturated disaccharides identifiable by HPLC [total area of peaks of ΔDiHS-OS, ΔDiHS-NS, ΔDiHS-6S, ΔDiHS-US, ΔDiHS-di(6,N)S, ΔDiHS-di(U,N)S, ΔDiHS-di(U,6)S and ΔDiHS-tri(U,6,N)S] as 100%.

The effective disaccharide yield is represented as a percentage by a proportion of the total area of peaks of the identifiable unsaturated disaccharides (ΔDiHS-OS, ΔDiHS-NS, ΔDiHS-6S, ΔDiHS-US, ΔDiHS-di(6,N)S, ΔDiHS-di(U,N)S, ΔDiHS-di(U,6)S and ΔDiHS-tri(U,6,N)S) in the total area of all the peaks detected by the HPLC analysis in the above disaccharide analysis method, multiplied by the enzymatic digestivity measured according to the following Test Method 4.

Test Method 3
[Measurement of Molecular Weight]

10 μl of a solution containing 3% (w/w) of a test substance was analyzed by HPLC gel filtration. The column used was a TSKgel-(G4000+G3000+G2500)PW$_{XL}$ (Tosoh Corp., φ 7.8×300 mm). The test substance was eluted by using 0.2 M sodium chloride as eluent at a flow rate of 0.6 ml/minute. A differential refractometer (Shimadzu Corp., Model AID-2A) was used to detect the test substance. The molecular weight was calculated by using heparin of a predetermined molecular weight (weight average molecular weight) as control (Kaneda et al., Biochem. Biophys. Res. Comm. (1996) 220, 108–112).

Test Method 4
[Measurement Method for Enzymatic Digestivity]

(1) Digestion with Glycosaminoglycan-degrading Enzymes 1.0 mg of a test substance was dissolved in 220 μl of 20 mM sodium acetate (pH 7.0) containing 2 mM calcium acetate. Glycosaminoglycan-degrading enzymes (20 mU each of heparinase and heparitinases I and II) were added thereto, and allowed to react at 37° C. for 2 hours.

(2) Analysis by Gel Filtration

20 μl of the solution obtained after enzymatic digestion according to the above (1) was analyzed gel filtration using HPLC. The column used was a TSKgel-(G4000+G3000+G2500)PW$_{XL}$ (Tosoh Corp., φ 7.8×300 mm). The test substance was eluted by using 0.2 M sodium chloride as an eluent at a flow rate of 0.6 ml per minute. A differential refractometer (Shimadzu Corp., Model AID-2A) was used to detect the test substance. The enzymatic digestivity was calculated as a percentage of the total area of peaks at retention times of 41.5 minutes (trisulfated unsaturated disaccharide), 42 minutes (disulfated unsaturated disaccharide), 43 minutes (monosulfated unsaturated disaccharide) and 45 minutes (unsaturated disaccharide without a sulfate group), relative to the total area of peaks at the retention times of 40 minutes (unsaturated tetrasaccharide), 41.5 minutes (trisulfated unsaturated disaccharide), 42 minutes (disulfated unsaturated disaccharide), 43 minutes (monosulfated unsaturated disaccharide) and 45 minutes (unsaturated disaccharide without a sulfate group).

Test Method 5
[Measurement Method for Activated Partial Thromboplastin Time (APTT)]

An injection syringe containing 3.2% sodium citrate was used to collect blood of 9-fold volume of the aqueous sodium citrate from the rat abdominal vena cava. The mixture was centrifuged at 4° C. at 1,000×g for 10 minutes to obtain plasma. 100 μl of the plasma and 100 μl of physiological saline containing a test substance at a predetermined concentration were dispensed in measuring cups and incubated at 37° C. for 1 minute. Then, 100 μl of Actin (trade name of Yoshitomi Pharmaceutical Industries, Ltd.) that had been maintained at 37° C. for 5 minutes beforehand was added thereto and incubated at 37° C. for further 2 minutes. Subsequently, coagulation was allowed to start by adding 100 μl of 0.02 M calcium chloride solution that had been preliminarily maintained at 37° C. The coagulation time was measured by using an automatic blood coagulation measurement apparatus (Baxter, Model AMELUNG KC10A).

Test Method 6
[Measurement Method for Thrombin Time (TT)]

100 μl of the plasma prepared according to the method explained for the APTT measuring method described above and 100 μl of physiological saline containing a test substance at a predetermined concentration were dispensed in measuring cups and incubated at 37° C. for 1 minute. Then, coagulation was started by adding 100 μl of thrombin (10 U/ml, Yoshitomi Pharmaceutical Industries, Ltd.) that had been preliminarily maintained at 37° C. for 5 minutes. The coagulation time was measured by using a coagulometer (Baxter, Model AMELUNG KC10A).

Test Method 7
[Measurement Method for Antithrombin Activity]

Three solutions, 350 μl of 20 mM Tris buffer (pH 7.4) containing 150 mM sodium chloride, 10 mM calcium chloride and 0.1% bovine serum albumin, 100 μl of bovine ATIII solution (1 U/ml in the same buffer) and 100 μl of a two-fold serial diluted aqueous solution of a test substance (sample), were mixed in the cooled state, and incubated at 37° C. for 2 minutes. To this solution, 50 μl of bovine thrombin solution (50 mU/ml in distilled water) was added, and incubated at 37° C. for 5 minutes. Then, to the mixture, 100 μl of a substrate solution (Boc-Val-Pro-Arg-MCA (Peptide Laboratory, Boc refers to tert-butyloxycarbonyl and MCA refers to 7-amino-4-methylcoumarin, 70 μM aqueous solution) was added, and the mixture was stirred and incubated at 37° C. for 3 minutes. Subsequently, the reaction was stopped by adding 300 μl of 30% acetic acid. Fluorescence intensity of the reaction mixture was measured at an excitation wavelength of 350 nm and a fluorescence wavelength of 444 nm. Blank 1 in which distilled water was used instead of the sample in the above reaction mixture composition and Blank 2 composed of a reaction mixture comprising only the substrate and the buffer were treated in the same manner, and fluorescence intensity thereof was measured.

The thrombin activity inhibition ratio was calculated according to the following equation, and inhibition ratios at test substance concentrations were plotted in a semilogarithmic graph to obtain a concentration exhibiting 50% inhibition ($IC_{50}$).

Thrombin activity inhibition ratio=$(1-(\Delta Fs/\Delta Fb))\times 100(\%)$ wherein, ΔFs represents (fluorescence intensity of sample-fluorescence intensity of Blank 1) and ΔFb represents (fluorescence intensity of Blank 2-fluorescence intensity of Blank 1).

Test Method 8
[Measurement Method for Hemorrhagic Activity]

A rat was anesthetized with ether, and then subcutaneously administered on its back with 0.4 ml of physiological saline containing 0.2 mg, 0.4 mg or 0.8 mg of each test substance per administration site. As for a negative control, 0.4 ml of physiological saline was subcutaneously administered per site. The rat was killed by bleeding 24 hours later. The skin surrounding each injection site was removed and the long and short diameters of the subcutaneous ecchymosis were measured by using a vernier caliper to calculate the area. The difference from the negative control group was determined by the Dunnett's multiple comparison test.

Test Method 9
[Measurement 1 for bFGF Activity-promoting Effect (with Addition of $NaClO_3$)]

A31 cells (BALB/c mouse 3T3 cells) subcultured in the DMEM (Asahi Techno Glass) containing 10% bovine serum were suspended in DMEM-ITS medium (ITS manufactured by GIBCO BRL, 10 mg/l of insulin, 5.5 mg/l of transferrin and 6.7 µg/l of selenious acid) containing 20 mM $NaClO_3$ and 2 ng/ml of human recombinant basic fibroblast growth factor (hrbFGF, Promega) at a density of $5\times10^4$ cells/ml. Each test substance was added to the cell suspension at a final concentration of 1 µg/ml. 100 µl of the cell suspension was seeded into each well of a 96-well microtiter plate and cultured. After cultured for 3 days, 20 µl of Celltiter 96AQ non-radioactive cell proliferation assay solution (Promega) was added to each well, and cultured at 37° C. for 2 hours. The cell proliferation of each well was quantified by using an absorptiometere to measure absorbance at a wavelength of 492 nm. The cell proliferation rate in the presence of each test substance was calculated by taking the cell proliferation rate in the presence of standard heparin as 100%, and the cell proliferation rate of the negative control (no test substance was added, but only phosphate-buffered physiological saline (PBS) was added as solvent) as 0%.

[Measurement 2 for bFGF Activity-promoting Effect (without Addition of $NaClO_3$)]

A31 cells (BALB/c mouse 3T3 cells) subcultured in the DMEM (Asahi Techno Glass) containing 10% bovine serum were suspended in the DMEM-ITS medium (ITS manufactured by GIBCO BRL, 10 mg/l of insulin, 5.5 mg/l of transferrin and 6.7 µg/l of selenious acid) containing 2 ng/ml of hrbFGF (Promega) at a density of $5\times10^4$ cells/ml. Each test substance was added to the cell suspension at a final concentration of 20 µg/ml. 100 µl of the cell suspension was seeded into each well of a 96-well microtiter plate and cultured. After cultured for 3 days, 20 µl of Celltiter 96AQ non-radioactive cell proliferation assay solution (Promega) was added to each well, and cultured at 37° C. for 2 hours. The cell proliferation of each well was quantified by using an absorptiometer to measure absorbance at a wavelength of 492 nm. The cell proliferation rate in the presence of each test substance was calculated by taking the cell proliferation rate in the presence of standard heparin as 100%, and the cell proliferation rate of the negative control (no test substance was added, but only phosphate-buffered physiological saline (PBS) was added as solvent) as 0%.

[Measurement 3 for bFGF Activity-promoting Effect (without Addition of $NaClO_3$/Primary Culture Cells)]

Under ether anesthesia, C57BL/6 mice (9-week old, female, Charles River) was shaved on its back and preliminarily sterilized cotton balls were embedded under the skin (2 sites/mouse). The cotton balls were removed together with granulation tissues 10 days later. The cotton balls were washed twice with a penicillin/streptomycin solution (penicillin: 200 U/ml, streptomycin: 200 µg/ml) and once with PBS. Then, the membrane covering the cotton balls was removed. The cotton balls were transferred into a tube with a solution containing 0.1% collagenase and 0.25% trypsin, and shaken in a thermostat at 37° C. for 1 hour. The treated solution was sieved through a cell strainer (+70 µm). RPMI1640 medium (Iwaki) containing 10% bovine serum was added thereto, and the mixture was slightly stirred and centrifuged at 2,000×g for 3 minutes. The obtained cells were washed with the same medium 3 times, re-suspended in the same medium at a density of $1\times10^5$ cells/ml, and seeded into a 10-cm petri dish. On the following day, cells not adhered were removed and the cells were cultured in a $CO_2$ incubator at 37° C. until a subconfluent state was obtained.

The subconfluent cells were separated from the petri dish by using a solution of 0.25% trypsin and 0.05% EDTA. The cells were washed by centrifugation and suspended in Basal ME/S-MEM medium (Gibco) containing 0.1% dialyzed bovine serum at $5\times10^4$ cells/ml. 100 µl of the cell suspension was dispensed in each well of a 96-well microtiter plate. Further, 50 µl of the Basal ME/S-MEM medium containing 4 µg/ml of hrbFGF (Promega) and 50 µl of the Basal ME/S-MEM medium containing Invention 2 were dispensed to each well, and the cells were cultured in the $CO_2$ incubator at 37° C. for 3 days. After the culture was completed, 15 µl of Cell Counting solution (Dojin) was added to each well and culture was continued for further 3 hours. Then, the absorbance of the medium was measured at 450 nm. As a negative control, a sample to which was added only the Basal ME/S-MEM medium as solvent, but not Invention 2, was used. As a positive control, used was a sample to which was used the Basal ME/S-MEM medium dissolving Standard H instead of Invention 2.

REFERENCE EXAMPLE 1
[Standard Heparin Used as Control in Examples]

As a standard heparin, heparin derived from swine small intestines (commercially available from SPL) was used. This heparin had the following physicochemical properties.

(1) The following disaccharide composition (molar %) obtained by the disaccharide analysis method according to the above Test Method 2 (the effective disaccharide yield: 85.5%).

TABLE 2

| ΔdiHS- | | | | | | | |
|---|---|---|---|---|---|---|---|
| OS | NS | 6S | US | di(6,N)S | di(U,N)S | di(U,6)S | tri(U,6,N)S |
| 3.9 | 2.3 | 3.8 | 1.8 | 11.4 | 6.4 | 1.5 | 68.9 |

(2) Anticoagulative activity of 160 IU/mg.
(3) Average molecular weight within the range of 13,000 to 15,000 Da determined by the above Test Method 3.

(4) Enzymatic digestivity determined by the above Test Method 4 of 89.8%.
(5) APTT of not less than 200 seconds measured by the APTT-measuring method of the above Test Method 5, when a solution containing 3 µg/ml of Standard H is used.
(6) TT of not less than 600 seconds measured by the TT-measuring method of the above Test Method 6, when a solution of 1 µg/ml of standard H is used.

Hereafter, this standard heparin is referred to merely as "Standard H".

REFERENCE EXAMPLE 2
Preparation of Control Glycosaminoglycan 1 (known Substance 1)

Control glycosaminoglycan 1 (referred to simply as "Control 1" hereafter) was prepared according to the method described in an example of WO96/01278. That is, 200 mg of heparin pyridinium salt (hereafter, "HepP") prepared as pyridinium salt from Standard H in a conventional manner was added to and dissolved in 20 ml of dehydrated pyridine. To the solution, 4 ml (about 4 g, 20-fold weight of HepP) of MTSTFA was added and the mixture was stirred at 95° C. for 2 hours. Then, to the mixture, 20 ml of water was added and the mixture was dialyzed using a Millipore ultrafiltration membrane (Millipore). The dialyzed solution was heated at 100° C. until the white turbidity disappeared. Subsequently, the solution was adjusted to pH 9 by addition of NaOH (1 N) and dialyzed against flowing water for 18 hours and against distilled water for 2 hours. The dialyzed solution was lyophilized to obtain 130 mg of powder of Control 1 (sodium salt).

REFERENCE EXAMPLE 3
Preparation of Control Glycosaminoglycan 2 (known Substance 2, Solvolysis+N-Re-sulfation)

Control glycosaminoglycan 2 (referred to simply as "Control 2" hereafter) was prepared according to the description of Example 1 of WO95/30424. That is, 50 mg of HepP was added to and dissolved in 10 ml of water. This solution was diluted with 90 ml of dimethyl sulfoxide, and the mixture was stirred on a hot water bath at 100° C. for 72 hours. 50 ml of 5% sodium hydrogencarbonate was added thereto and the mixture was cooled. Then, the solution was dialyzed twice against 1 l of 0.1 M sodium acetate solution each for 12 hours and thoroughly dialyzed against distilled water.

To this dialyzed solution, aqueous sodium carbonate at a concentration of 0.1 M and further 5 molar equivalents of pyridine/SO$_3$ were added and the mixture was stirred at 60° C. for 24 hours. In the period of 24 hour, 5 molar equivalents of pyridine/SO$_3$ was added twice every 8 hours. Then, the solution was dialyzed against flowing water for 18 hours and against distilled water for 2 hours. The dialyzed solution was filtered and lyophilized to obtain 47.5 mg of powder of Control 2 (sodium salt).

EXAMPLE 1
[Preparation of Glycosaminoglycan of the Present Invention Etc.]

HepP and MTSTFA were added to pyridine, and the mixture was stirred, heated and incubated for a certain period of time under each of the reaction conditions described in the following Table 3. The vessel containing the reaction mixture was cooled on ice. Then, the mixture was concentrated 10-fold by using a rotary evaporator under reduced pressure and then 2-fold volume of distilled water was added thereto. Further, the mixture was placed under reduced pressure by using a rotary evaporator until the white turbidity disappeared, and dialyzed against flowing water for 48 hours and against distilled water for 2 hours. The dialyzed solution was passed through a column packed with an Amberlite IR-120B (H$^+$ form) resin (Organo Corp.) equilibrated with distilled water, and only the acidic fraction was pooled among the collected fractions. This acidic fraction was adjusted to pH 9 by addition of NaOH (1 N), and dialyzed against flowing water for 18 hours and against distilled water for 2 hours. The dialyzed solution was lyophilized to obtain each of the target preparations (sodium salt) as powder.

The obtained preparations (the glycosaminoglycans of the present invention 1 to 4 (Inventions 1 to 4) and the control glycosaminoglycans 3 to 6 (Controls 3 to 6)), and conditions used for each preparation are shown in Table 3.

TABLE 3

| | | MTSTFA | | Heating (oil bath) | | |
| | | Amount of | Weight ratio | | | |
| Substance | HepP Used | Amount Used | to HepP | Temp. | Retention time | Yield |
| --- | --- | --- | --- | --- | --- | --- |
| Invention 1 | 0.5 g | 5 g | 10-fold | 110° C. | 120 min. | 385 mg |
| Invention 2 | 5 g | 50 g | | | | 3.3 g |
| Control 3 | | | | | 15 min. | 3.9 g |
| Control 4 | | | | | 30 min. | 3.7 g |
| Control 5 | | | | | 60 min. | 3.4 g |
| Invention 3 | 50 g | 500 g | | | 120 min. | 33.0 g |
| Invention 4* | 500 g | 5000 g | | | | 307.0 g |
| Control 6 | 5 g | 100 g | 20-fold | 95° C. | 120 min. | 3.5 g |

*A steam jacket was used for heating.

Different reaction scales were used for Inventions 1 to 4. The same reaction scale as that of Invention 2 was used for Controls 3 to 5, but the reaction time was altered to obtain the controls. The same amount of HepP as for Invention 2 was used for Control 6, but MTSTFA as the silylating agent was used in 20-fold amount and the reaction temperature was lowered to obtain the control.

The average molecular weight was measured according to Test Method 3. As a result, it has been revealed to be about 12,500 Da for all the substances and it was found that the molecular weight has not been substantially reduced.

EXAMPLE 2

(1) Enzymatic Digestivity

The enzymatic digestivity of Standard H, Inventions 1 to 4 and Controls 1, 2 and 6 was measured according to the method described in Test Method 4. The 6-desulfation ratio was also calculated for the substances except for Standard H according to the method described in Test Method 1 (Table 4). The 6-desulfation ratio of Control 1 shown in Table 4 was quoted from the value given in WO96/01278.

TABLE 4

| Substance | Enzymatic digestivity | 6-Desulfation ratio |
|---|---|---|
| Standard H | 89.8% | — |
| Invention 1 | 81.5% | 100% |
| Invention 2 | 81.0% | 100% |
| Invention 3 | 82.0% | 100% |
| Invention 4 | 73.0% | 100% |
| Control 1 | 35.0% | 81.2%* |
| Control 2 | 81.0% | 100% |
| Control 3 | Not measured | 56.7% |
| Control 4 | Not measured | 70.0% |
| Control 5 | Not measured | 90.0% |
| Control 6 | 81.8% | 80.3% |

*The 6-desulfation ratio given in WO96/01278.

It was revealed that the high enzymatic digestivity and high 6-desulfation ratio were achieved in the glycosaminoglycans of the present invention (Inventions 1 to 4) and Control 2.

(2) Disaccharide Composition

The disaccharide composition was determined for Standard H, Inventions 1 to 4 and Controls 1, 2 and 6 according to the enzymatic disaccharide analysis method described in Test Method 2 (Table 5).

TABLE 5

| Substance | ΔDiHS- | | | | | | | | Effective disaccharide yield |
|---|---|---|---|---|---|---|---|---|---|
| | 0S | NS | 6S | US | di(6, N)S | di(U, N)S | di(U, 6)S | tri(U, 6, N)S | |
| Standard H | 3.9 | 2.3 | 3.8 | 1.8 | 11.4 | 6.4 | 1.5 | 68.9 | 85.5% |
| Glycosaminoglycan of the present invention | | | | | | | | | |
| Invention 1 | 11.8 | 25.2 | 1.0 | 6.0 | 1.3 | 54.7 | 0 | 0 | 81.5% |
| Invention 2 | 9.3 | 25.9 | 0 | 6.7 | 4.7 | 53.4 | 0 | 0 | 82.0% |
| Invention 3 | 11.5 | 30.4 | 2.5 | 4.9 | 2.3 | 48.0 | 0 | 0 | 81.8% |
| Invention 4 | 11.8 | 22.6 | 2.4 | 4.5 | 1.6 | 57.1 | 0 | 0 | 65.3% |
| Known substance (WO96/01278) | 6.8 | 10.2 | 0 | 2.6 | 5.7 | 73.0 | 0 | 1.7 | 32.4% |
| Control 1 | | | | | | | | | |
| Control 6 | 9.2 | 12.2 | 1.1 | 5.0 | 4.7 | 54.9 | 0 | 8.2 | 81.5% |
| Known substance (WO95/30424) | 13.3 | 65.2 | 0 | 0 | 0 | 21.5 | 0 | 0 | 81.0% |
| Control 2 | | | | | | | | | |

Note:
0 indicates that the value was below the detection limit.
Unit: molar %

As a result, Control 2 prepared by the desulfation method using solvolysis exhibited a disaccharide composition distinctly different from that of other substances. It was also found that the glycosaminoglycans of the present invention had less sulfate groups at the 6-position compared with Standard H, Control 1 and Control 6. Further, the glycosaminogycans of the present invention were characterized by that no trisulfated unsaturated disaccharide (ΔDiHS-(U,6,N)triS) was detected.

EXAMPLE 3
Measurement of Endotoxin Concentration

Endotoxins contaminated in the glycosaminoglycan preparation of the present invention were measured by calorimetric quantification using a Toxicolor-LS-50M set (Seikagaku Corporation). The Toxicolor-Et-2 (Seikagaku Corporation) was used as standard endotoxin.

That is, Invention 5 was prepared according to the method used for preparing Invention 2 described in Example 1 by using endotoxin-free instruments, pyridine and distilled water. Then, 50 μl of (1) aqueous solution in which Invention 5 was diluted at a concentration of 2 mg/ml and (2) aqueous solution of (1) containing endotoxin at 0.212 EU/mL were each dispensed in wells of an endotoxin-free microtiter plate. Similarly, (3) 50 μl of aqueous solution containing Et-2 at 0.424 EU/ml as a standard solution and (4) 50 μl of distilled water (endotoxin-free) as a blank were each dispensed in wells of an endotoxin-free microtiter plate. 50 μl of the main reagent contained in the Toxicolor-LS-50M set was added to each well to which (1) to (4) were dispensed, and the plate was immediately set on a well reader SK601 (sold by Seikagaku Corporation). Time course of the absorbance (mAbs/min) at a measurement wavelength of 405 nm and a control wavelength of 492 nm during the reaction at 37° C. for 30 minutes was measured to obtain an absolute calibration curve, which was used for calculation of endotoxin concentration.

Since it was possible that Invention 5 itself had inhibitory activity or hyperactivity against LAL reagents, an addition yield was obtained from a measured value corresponding to an added endotoxin unit amount according to the following equation, and an actual measured value was corrected by multiplying by it.

{(Measured value with addition)−(Measured value without addition)}/(Added endotoxin concentration)

The endotoxin activity in an aqueous solution of 10 mg/ml of Invention 5 thus obtained was 0.427 EU/ml. That is, the contaminated endotoxin amount of Invention 5 was 0.0427 EU/mg. Thus, it was revealed that a glycosaminoglycan preparation of the present invention with a contaminated endotoxin amount that was sufficiently low as pharmaceutical preparations could be prepared only by preparing it by the preparation method of the present invention.

EXAMPLE 4
Measurement of Pyridine Content

The content of pyridine that remained in the glycosaminoglycan in the present invention was measured. That is, Invention 3 (20 mg) was added to 5 N NaOH (1 ml), and this solution was sonicated for 5 minutes. To this solution, 1 ml of dimethyl ether was added and the mixture was vigorously stirred for 2 minutes. Then, the solution was centrifuged at 3,000×g for 10 minutes to be separated into an upper layer (1) (organic layer) and a lower layer (1) (aqueous layer). To the lower layer (1), 1 ml of dimethyl ether was further added and the mixture was vigorously stirred. Then, the solution was centrifuged under the same conditions as above to be separated into an upper layer (2) (organic layer) and a lower layer (2) (aqueous layer). The lower layer (2) was discarded. The upper layer (1) and the upper layer (2) were combined to obtain 2 ml of an extract (1).

To the extract (1) obtained as described above, 400 µl of 2 N HCl was added and the mixture was vigorously stirred for 2 minutes. This mixture was centrifuged at 3,000×g for 10 minutes to be separated into an upper layer (3) (organic layer) and a lower layer (3) (aqueous layer). The upper layer was discarded. To the lower layer (3), 5 N NaOH (800 µl) and further 300 µl of dichloromethane were added, and then the mixture was vigorously stirred for 2 minutes. The solution was centrifuged at 3,000×g for 10 minutes to be separated into an upper layer (4) (aqueous layer) and a lower layer (4) (organic layer). The upper layer (4) was discarded. 1 µl of the lower layer (4) was analyzed by gas chromatography.

GC-18APFSC (Shimadzu Corp.) was used for the gas chromatography, and DB-5 ms (φ 0.25 mm (I.D. 0.5 µm)×30 m: J&W) was used as a column. Helium was used as a mobile phase. The flow rate was set to be 22 cm/sec at 80° C. and the column was maintained at 80° C. for 1 minute. Then, the column oven temperature was increased at a rate of 10° C. per minute up to 120° C. for elution. Detection was performed at 300° C. by using FID (Flamed Ionized Detection). The calibration curve was created by analyzing 1 µl of methanol containing pyridine at concentrations of 20, 40, 60, 80 and 100 ppm. Moisture content of Invention 3 was set to be 10% for calculation. For Invention 3, extraction and quantification of residual pyridine content were performed twice. As a result, the two measured values of the residual pyridine content were 73.1 ppm and 70.3 ppm. Both values were considerably lower than 200 ppm, which is the regulated value for residual pyridine content in pharmaceuticals.

EXAMPLE 5
[Structural Analysis by $^{13}$C-Nuclear Magnetic Resonance Spectroscopy]

Figure 2:
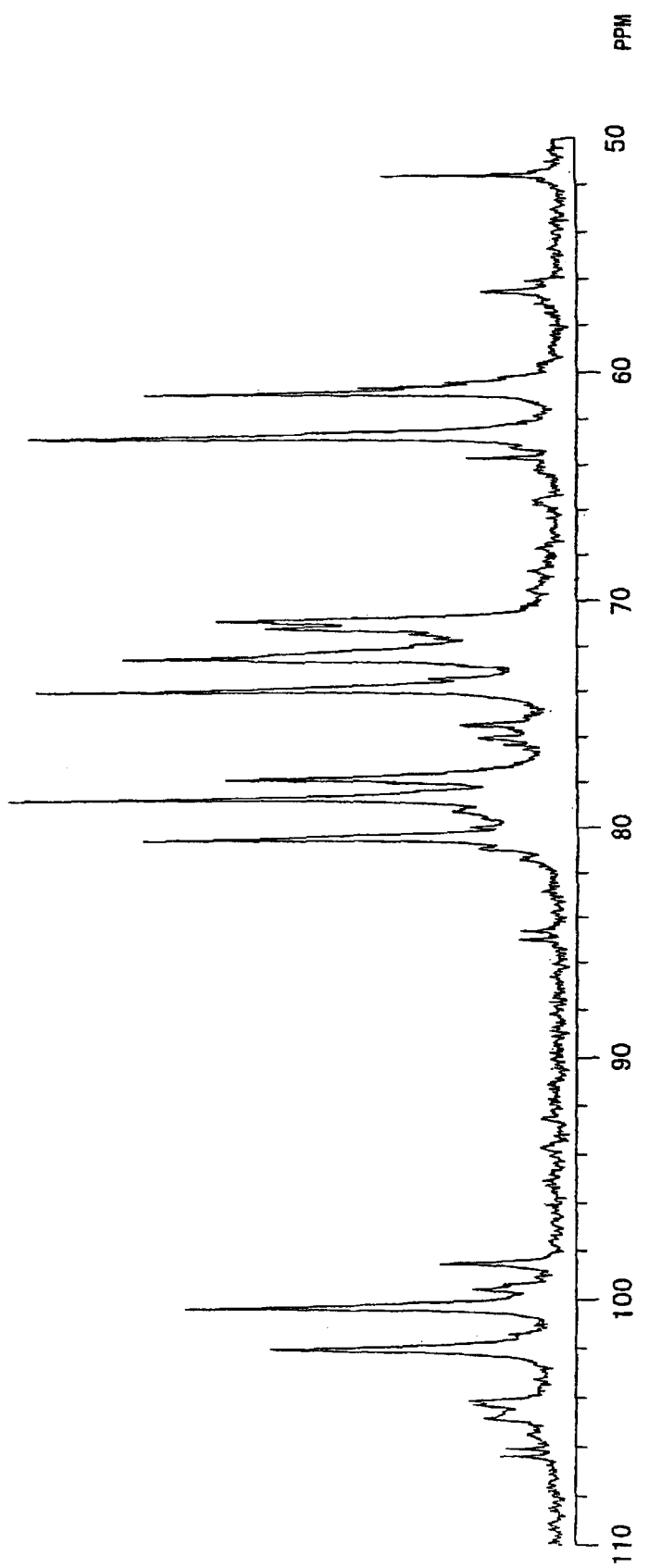
FIG. 2 shows $^{13}$C-MNR spectrum of a glycosaminoglycan of the present invention (Invention 1).
Figure 3:
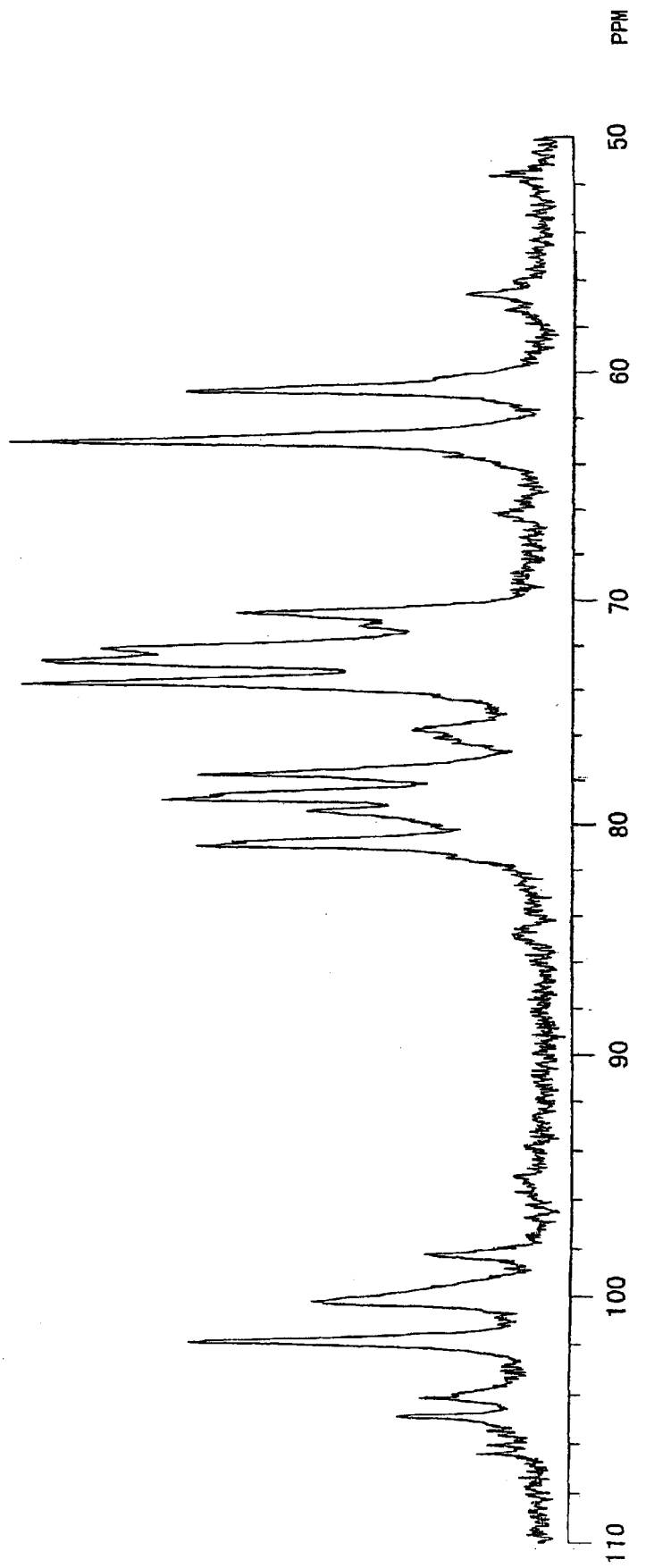
FIG. 3 shows $^{13}$C-MNR spectrum of a glycosaminoglycan of the present invention (Invention 3).
Figure 4:
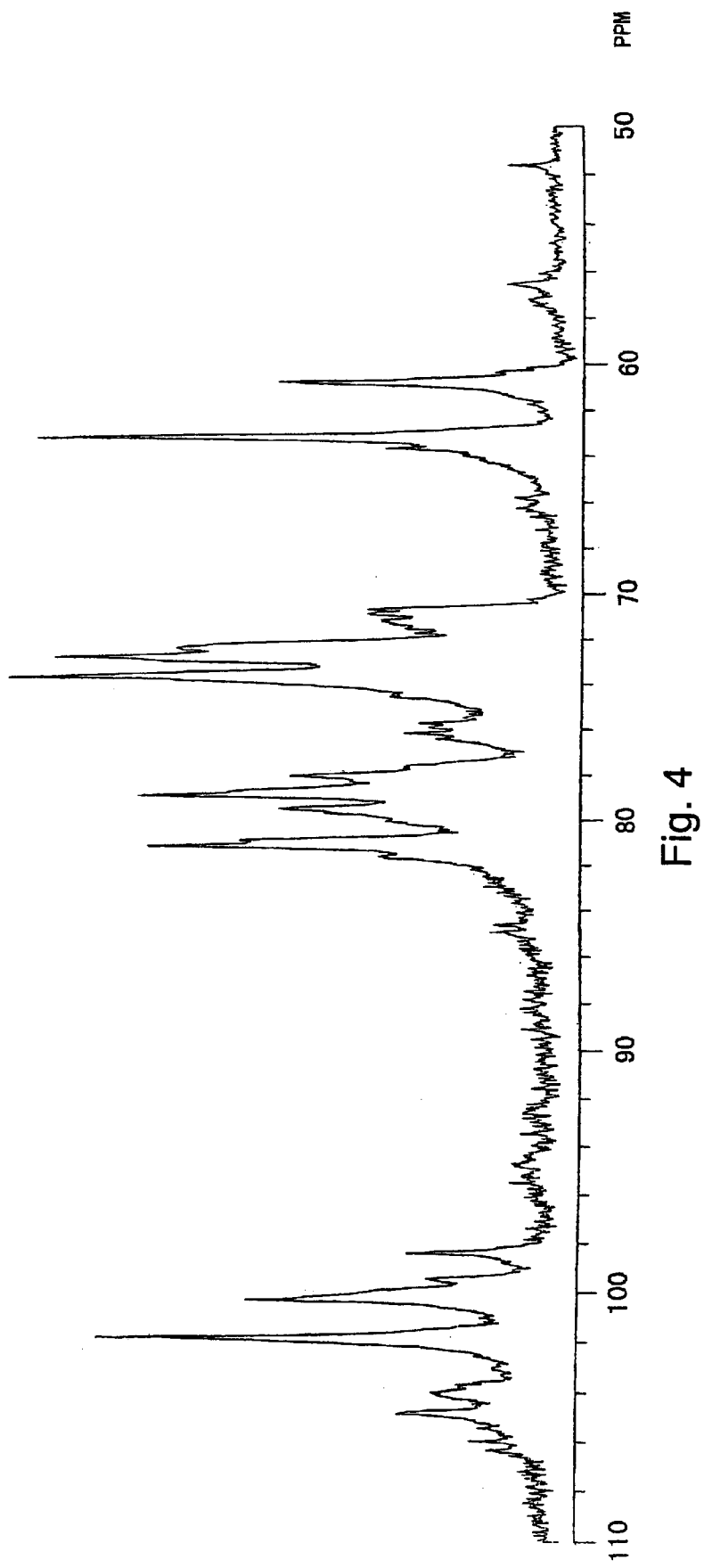
FIG. 4 shows $^{13}$C-MNR spectrum of a glycosaminoglycan of the present invention (Invention 4).

Standard H, Inventions 1 to 4 and Controls 3 to 5 were analyzed by $^{13}$C-nuclear magnetic resonance spectroscopy ($^{13}$C-NMR) (Standard H: FIG. 1 (1), Invention 1: FIG. 2, Invention 2: FIG. 1 (5), Invention 3: FIG. 3, Invention 4: FIG. 4, Control 3: FIG. 1 (2), Control 4: FIG. 1 (3), Control 5: FIG. 1 (4)). An NMR spectrometer, Model QE300 (GE), was used for the $^{13}$C-NMR spectroscopy. A 5% (w/v) solution of each test substance was prepared in deuterium oxide. Measurement was performed by using methanol, which showed chemical shift of 51.66 ppm when TSP (Wako Pure Chemicals Industries, Ltd.) was used as a standard (0 ppm), as an internal standard, at a measuring temperature of 80° C., with a pulse width of 60° and an integration number of 90,000 times. The chemical shifts of the signals of Standard H, Inventions 1 to 4 are as follows (Table 6).

TABLE 6

| | Glucosamine residue | | | | | | Uronic acid (iduronic acid) residue | | | | |
| Substance | C-1 | C-2 | C-3 | C-4 | C-5 | C-6 | C-1 | C-2 | C-3 | C-4 | C-5 |
| --- | --- | --- | --- | --- | --- | --- | --- | --- | --- | --- | --- |
| Standard H | 99.4 | 60.5 | 72.4 | 79.1 | 72.2 | 69.1 | 101.9 | 78.7 | 71.8 | 78.8 | 72.0 |
| Invention 1 | 100.3 | 60.6 | 72.3 | 80.4 | 73.7 | 62.6 | 102.0 | 78.4 | 70.7 | 77.6 | 71.0 |
| Invention 2 | 100.3 | 60.8 | 72.4 | 80.4 | 73.8 | 62.6 | 102.0 | 77.7 | 70.7 | 78.6 | 71.0 |
| Invention 3 | 100.2 | 60.5 | 72.5 | 80.8 | 73.5 | 62.9 | 101.8 | 78.5 | 70.5 | 77.8 | 71.0 |
| Invention 4 | 100.2 | 60.7 | 72.3 | 80.8 | 73.4 | 63.0 | 101.7 | 78.5 | 70.6 | 77.9 | 71.2 |

Unit: ppm

The results of $^{13}$C-NMR show that the signal of C-6 of the glucosamine residue is detected at 69.1 ppm (signal of carbon atom at the 6-position with a sulfate group) and 62.6 to 63.0 ppm (signal of carbon atom at the 6-position without a sulfate group). Shown below (Table 7) are the results of calculation of the ratio of the glucosamine residue with 6-position not sulfated (6-position non-sulfated GlcN ratio) and the 6-position desulfation ratio (de-6S ratio) of the glucosamine residue based on Standard H of each sample (Inventions 1 to 4 and Controls 3 to 5) by using the above signal intensities and the ratios of the signal intensities.

TABLE 7

| Test substance | Signal intensity at 69.1 ppm | Signal intensity at 62.6 ppm | 6-Position non-sulfated GlcN ratio (%) | De-6S ratio (%) |
| --- | --- | --- | --- | --- |
| Standard H | 57.0 | 10.2 | 15.2 | 0 (Standard) |
| Control 3 | 34.5 | 59.6 | 63.3 | 56.7 |
| Control 4 | 19.0 | 84.9 | 81.7 | 78.4 |
| Control 5 | 7.1 | 80.1 | 91.9 | 90.5 |
| Invention 1 | 0* | 94.3 | 100 | 100 |
| Invention 2 | 0* | 93.2 | 100 | 100 |
| Invention 3 | 0* | 90.8 | 100 | 100 |
| Invention 4 | 0* | 62.9 | 100 | 100 |

Note: 0* indicates the value was below the measurement limit.

As is evident from these results, almost 100% 6-position desulfation was achieved by the reaction for approximately 2 hours when incubated at 110° C. under the above desulfation conditions.

Figure 5:
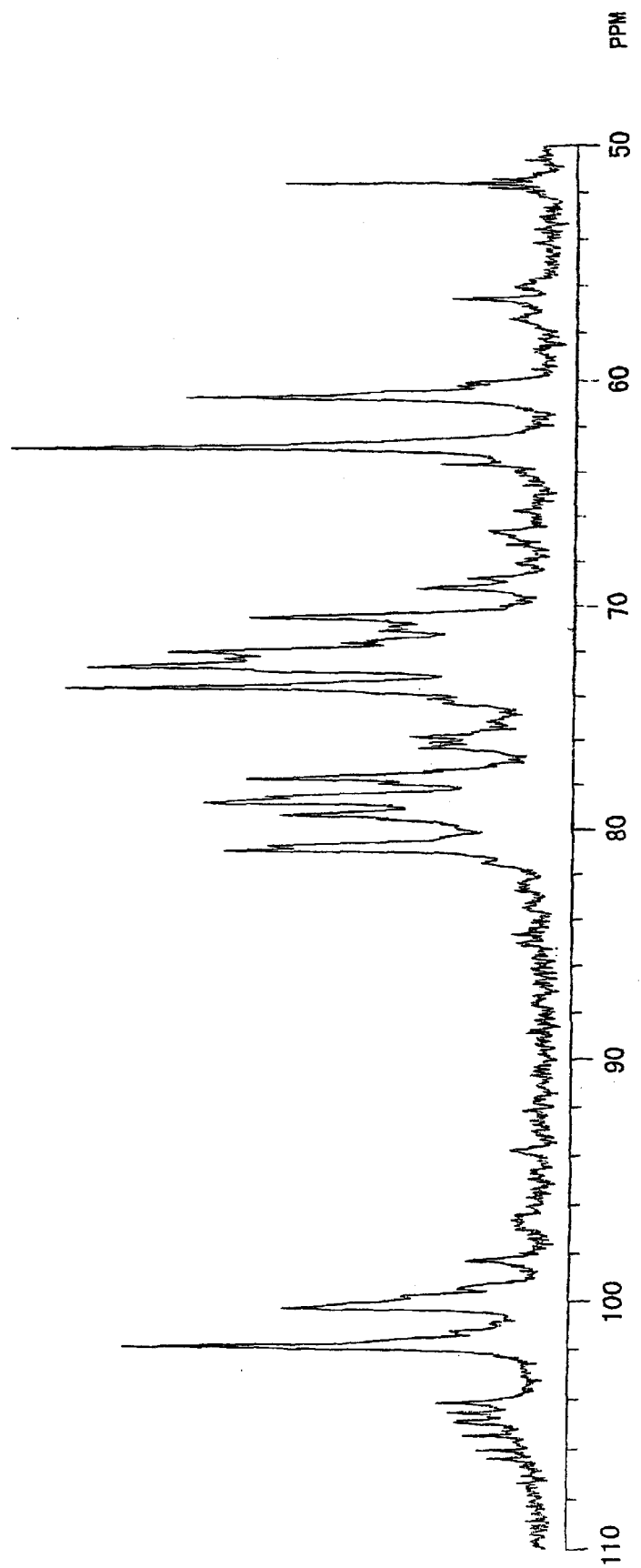
FIG. 5 shows $^{13}$C-MNR spectrum of a control glycosaminoglycan (Control 1).

Control 1 and Control 2 were analyzed by using $^{13}$C-NMR spectroscopy as described above. For Control 1, the peak position of each carbon atom was detected at positions near those of Inventions 1 to 4, but characteristic peaks that were not observed in any of Inventions 1 to 4 and Standard H were detected at 67 ppm and 96.5 to 97.0 ppm (continuously) (FIG. 5). Since these characteristic peaks were not observed in Control 3, Control 4 and Control 5 (substances obtained by altering the reaction time in preparation of Invention 2), it was revealed that Control 1 had a different structure from that of the glycosaminoglycans of the present invention or substances obtained by altering the 6-position desulfation reaction time.

Figure 6:
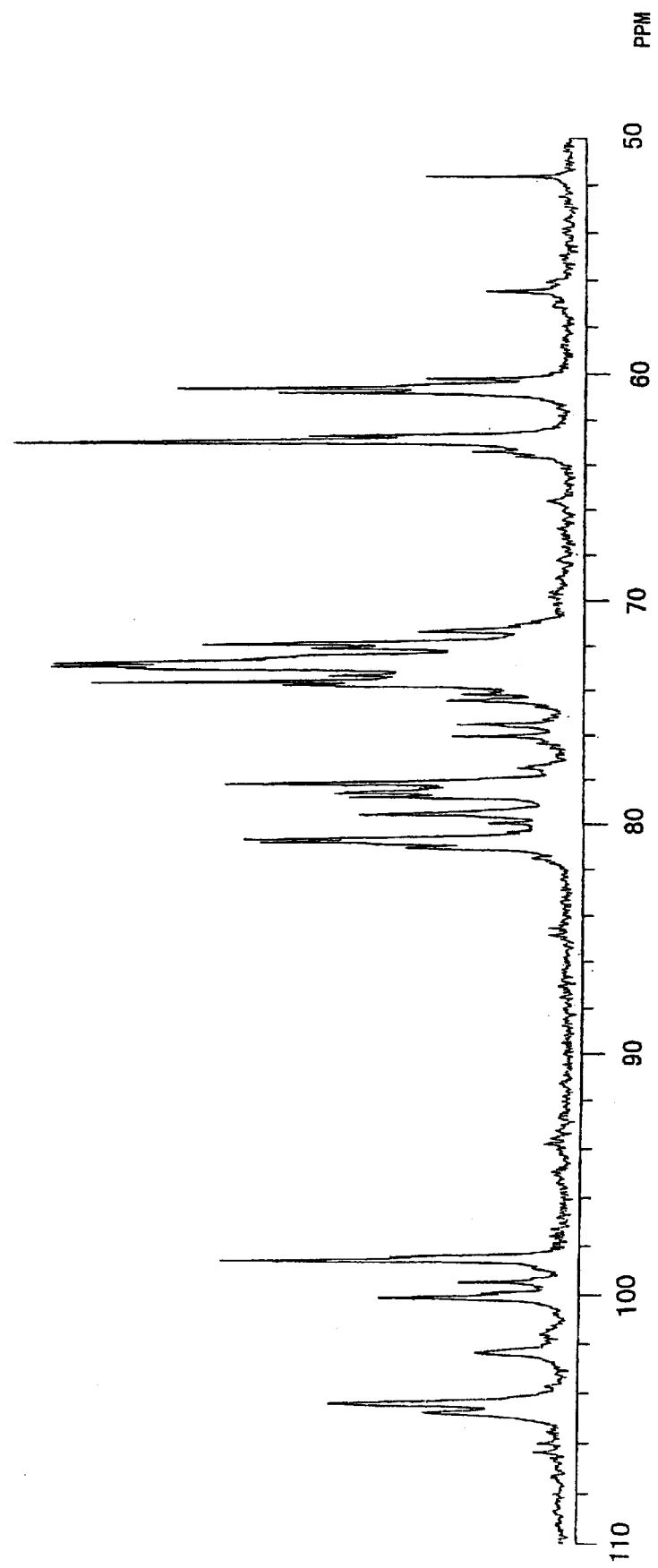
FIG. 6 shows $^{13}$C-MNR spectrum of a control glycosaminoglycan (Control 2).

As for Control 2, it was found that the peak of carbon atom at the 3-position of the uronic acid is not observed in the range of 70.0 to 71.0 ppm, which was observed for Standard H and Inventions 1 to 4 (FIG. 6). Furthermore, when peaks around 98.3 ppm, 100 ppm and 102 ppm observed for the heparin structure were compared, the peak around 98.3 ppm was the highest, which makes the chart characteristic. These results also demonstrated that Control 2 also had a different structure from that of the glycosaminoglycans of the present invention.

EXAMPLE 6
[Measurement of Anticoagulative Activity]

(1) Measurement of Activated Partial Thromboplastin Time (APTT)

APTT of Standard H, Invention 2, Control 4 and Control 5 was measured according to the method described in Test Method 5 (Table 8). As a result, it was found that APTT was prolonged in Standard H, Control 4 and Control 5, whereas Invention 2 showed little action to prolong APTT. Since the 6-position desulfation ratios for Control 1 and Control 6 were between those of Control 4 and Control 5, it was predicted that they would intermediate anticoagulative activity between Control 4 and Control 5.

TABLE 8

| Concentration (μg/ml) | Standard H | Control 4 | Control 5 | Invention 2 |
| --- | --- | --- | --- | --- |
| 0.01 | 25 | 25 | 26 | 24 |
| 0.03 | 26 | 24 | 23 | 26 |
| 0.1 | 27 | 25 | 24 | 25 |
| 0.3 | 36 | 27 | 26 | 24 |
| 1 | 98 | 26 | 25 | 24 |
| 3 | >600 | 34 | 26 | 27 |
| 10 | — | 48 | 35 | 25 |
| 30 | — | 96 | 52 | 36 |
| 100 | — | >600 | 102 | 51 |

Note:
— indicates "not measured".
Unit: second (2) Measurement of Thrombin Time (TT)

TT of Standard H, Invention 2, Control 4 and Control 5 was measured according to the method described in Test Method 6 (Table 9). As a result, it was found that TT was prolonged in Standard H, Control 4 and Control 5, whereas Invention 2 showed no action to prolong TT. Since the 6-position desulfation ratios of Control 1 and Control 6 were between those of Control 4 and Control 5, it was predicted that they would show intermediate anticoagulative activity between Control 4 and Control 5.

TABLE 9

| Concentration (μg/ml) | Standard H | Control 4 | Control 5 | Invention 2 |
| --- | --- | --- | --- | --- |
| 0.01 | 17 | 15 | 15 | 14 |
| 0.03 | 34 | 16 | 15 | 16 |
| 0.1 | 37 | 13 | 16 | 15 |
| 0.3 | 75 | 16 | 16 | 17 |
| 1 | >600 | 18 | 17 | 16 |

TABLE 9-continued

| Concentration (μg/ml) | Standard H | Control 4 | Control 5 | Invention 2 |
| --- | --- | --- | --- | --- |
| 3 | — | 23 | 16 | 16 |
| 10 | — | 35 | 17 | 18 |
| 30 | — | 385 | 53 | 16 |
| 100 | — | >600 | 96 | 17 |

Note:
— indicates "not measured".
Unit: second (3) Measurement of Antithrombin Activity Antithrombin activity of Standard H, Invention 2 and Control 1 was measured according to the method described in Test Method 7 (Table 10). The results revealed that antithrombin activity of Invention 2 was substantially lowered compared with Standard H and Control 1.

TABLE 10

| Test substance | Antithrombin activity ($IC_{50}$, ng/ml) |
| --- | --- |
| Standard H | 8.75 |
| Invention 2 | $1.22 \times 10^5$ |
| Control 1 | $8.84 \times 10^3$ |

EXAMPLE 7
[Hemorrhagic Activity of Glycosaminoglycan of the Present Invention]

Hemorrhagic activity of Standard H and Invention 2 was measured according to the method described in Test Method 8 (Table 11). The results revealed that Invention 2 had completely lost the hemorrhagic activity.

TABLE 11

| Test substance | Ecchymosis area $mm^2$ (bleeding frequency) | | | |
| --- | --- | --- | --- | --- |
| | 0.0 mg per wound | 0.2 mg per wound | 0.4 mg per wound | 0.8 mg per wound |
| Physiological saline | 0 ± 0 (0/7) | — | — | — |
| Standard H | — | 179 ± 82 (7/7) | 209 ± 35 (7/7) | 193 ± 56 (7/7) |
| Invention 2 | — | 0 ± 0 (0/7) | 0 ± 0 (0/7) | 0 ± 0 (0/7) |

Note: — indicates "not measured".

EXAMPLE 8
[Wound Healing-promoting Activity of Glycosaminoglycan of the Present Invention for Wounds of Healthy Skin]

Figure 7:
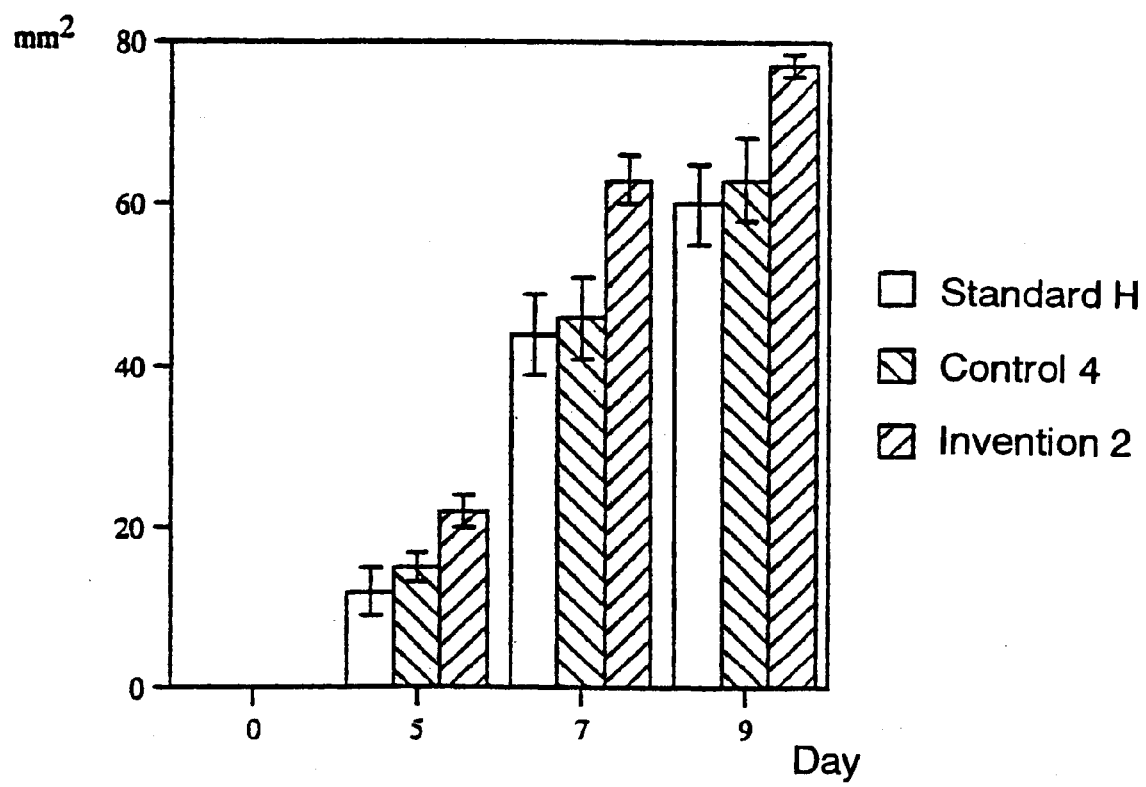
FIG. 7 shows healthy skin wound healing-promoting activity of the glycosaminoglycan of the present invention (Invention 2).
Figure 8:
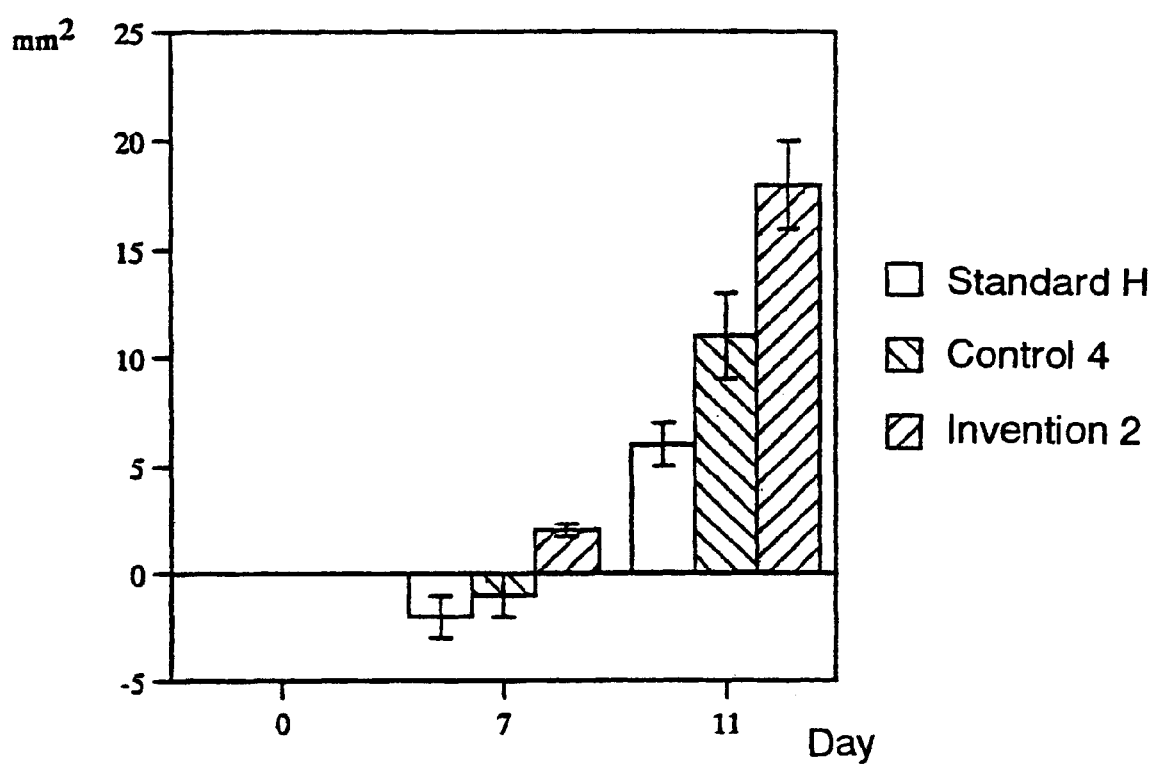
FIG. 8 shows diabetic skin ulcer healing-promoting activity of the glycosaminoglycan of the present invention (Invention 2).

Wound healing-promoting activity of the glycosaminoglycan of the present invention for wounds of healthy skin was examined by using healthy rats. That is, a healthy rat was shaved on its back, and the skin was dissected to a subcutaneous region by using an ophthalmological trephine of φ 8 mm. The skin was removed by using ophthalmological scissors and tweezers to create two defective wounds on its back. Then, oily ointments, each containing 0.5% by weight of Standard H, Invention 2 or Control 4, were prepared, and 0.1 g of each ointment was applied every day to compare the degrees of wound healing based on healed areas. The rat was statically placed under ether anesthesia, then photos of the defective portions were taken with a constant focal distance. The skin defective portions were measured on the photo prints by using an image analysis system to perform the measurement. Each healed area was obtained by subtracting the area at each measurement from the area immediately after the defective portion was created. The statistical analysis was performed by the Tukey's multiple comparison test. As a result, remarkable skin wound healing-promoting activity was observed in the group of animals to which the ointment prepared by using Invention 2 was applied (FIG. 7).

EXAMPLE 9
[Diabetic Skin Ulcer Healing-promoting Activity of Glycosaminoglycan of the Present Invention]

The diabetic skin ulcer healing-promoting activity of the glycosaminoglycan of the present invention was examined by using mice with hereditary diabetes (db/db mice (female): Japan Clare). That is, a mouse with hereditary diabetes was shaved on its back, and the skin was dissected to a subcutaneous region by using an ophthalmological trephine of $\phi$ 8 mm. The skin was removed by using ophthalmological scissors and tweezers to create two defective wounds on its back. Then, 50 $\mu$l of physiological saline containing 1% (w/w) of Standard H, Invention 2 or Control 4 was dropped every day to compare the degrees of wound healing. The rat was statically placed under ether anesthesia, then photos of the defective portions were taken with a constant focal distance. The skin defective portions were measured on the photo prints by using an image analysis system to perform the measurement. Each healed area was obtained by subtracting the area at each measurement from the area immediately after the defective portion was created. The statistical analysis was performed by the Tukey's multiple comparison test. As a result, it was revealed that Invention 2 statistically significantly promoted the healing after the 11 th day from the start of the administration although no remarkable difference was observed in any test substances for the first 7 days.

EXAMPLE 10
[Measurement of Affinity for bFGF of Glycosaminoglycan of the Present Invention]

Affinity of the glycosaminoglycan of the present invention for the cell proliferation factor was measured. That is, 0.2 mg of Invention 2 was dissolved in 100 $\mu$l of 50 mM sodium hydrogencarbonate buffer (pH 8.5). An aqueous solution containing 74 $\mu$g of NHS-LC-biotin (succinimidyl-6-(biotineamide)-hexanoate, Pierce) was added thereto, and the mixture was allowed to react at room temperature for 30 minutes. Subsequently, to the solution, 2.5-fold volume of ethanol was added, and the precipitated and biotinylated Invention 2 was collected by centrifugation. This biotinylated Invention 2 was immobilized on an avidinylated sensor chip (BIAcore AB, SA). bFGF dissolved in a liquid phase was brought into contact with the sensor chip surface, and then the interaction between Invention 2 and bFGF was analyzed by two kinds of methods, the affinity and kinetics analysis method and the steady-state analysis method, both using the surface plasmon effect.

As a result, the association rate constants ($K_a$) obtained by the former analysis method were 1.3 ($M^{-1}S^{-1}10^{-6}$) and 1.0 ($M^{-1}S^{-1}10^{-6}$) for Standard H used as control and Invention 2, respectively. The dissociation rate constants ($K_d$) were 4.8 ($S^{-1}10^3$) and 5.3 ($S^{-1}10^3$) for Standard H and Invention 2, respectively. The dissociation constants ($K_D$) calculated from these results were 4.1 nM and 4.3 nM for Standard H and Invention 2, respectively.

The dissociation constants ($K_D$) obtained by the latter analysis method were 23 nM and 24 nM for Standard H and Invention 2, respectively.

It is evident from these results that affinity of Invention 2 for bFGF is substantially the same as that of Standard H.

EXAMPLE 11
[Measurement of bFGF Activity-promoting Effect of Glycosaminoglycan of the Present Invention (with Addition of $NaClO_3$)]

The bFGF activity-promoting effect of Invention 2 was measured according to [Measurement 1 for bFGF activity-promoting effect] described in Test Method 9. Similarly, bFGF activity-promoting effects of Control 1 and Control 2 were also measured according to the same method. As a result, it was found that Invention 2 had the same degree of BFGF activity-promoting effect as that of Standard H (Table 12). It was also found that Control 1 had about 26% of bFGF activity-promoting effect compared with that of Standard H, that is, not more than ¼ of that of Invention 2. This suggested that the structural difference revealed by $^{13}$C-NMR caused the difference of the bFGF activity-promoting effect.

TABLE 12

| Substance | BFGF activity-promoting effect |
| --- | --- |
| Standard H | 100 |
| Invention 2 | 108 |
| Control 1 | 26 |
| Control 2 | 61 |

EXAMPLE 12
[Measurement 2 for bFGF Activity-promoting Effect of Glycosaminoglycan of the Present Invention (without Addition of $NaClO_3$)]

The BFGF activity-promoting effect of the glycosaminoglycan of the present invention (Invention 2) was measured according to [Measurement 2 for bFGF activity promoting effect] described in Test Method 9. Control 2 was used as a comparative control. As a result, it was found that Invention 2 had the same degree of bFGF activity-promoting effect as that of Standard H (Table 13). It was also revealed that the bFGF activity-promoting effect of Control 2 was not more than a half of that of Invention 2.

TABLE 13

| Substance | BFGF activity-promoting effect |
| --- | --- |
| Standard H | 100 |
| Invention 2 | 89.9 |
| Control 2 | 31.2 |

EXAMPLE 13
[Measurement 3 for bFGF Activity-promoting Effect of Glycosaminoglycan of the Present Invention (without Addition of $NaClO_3$/Primary Culture Cell)]

The bFGF activity-promoting effect of the glycosaminoglycan of the present invention (Invention 2) on primary culture cells was measured according to [Measurement 3 for bFGF activity-promoting effect] described in Test Method 9. Standard H was used as a comparative control. As a result, it was found that Invention 2 had 75% of bFGF activity-promoting effect of Standard H on primary culture cells (Table 14).

TABLE 14

| Substance | bFGF activity-promoting effect |
|---|---|
| Standard H | 100 |
| Invention 2 | 75 |

EXAMPLE 14
[Measurement of Affinity for Fructose 1,6-Bisphosphate Aldolase of Glycosaminoglycan of the Present Invention]

The affinity between fructose 1,6-bisphosphate aldolase (hereafter referred to as "FPA"), which is a key enzyme of the glycolysis pathway in respiration, and the glycosaminoglycan of the present invention was measured by affinity chromatography wherein a column for FPLC packed with an affinity gel carrier prepared according to the method of Sasaki et al. (J. Chromatogr. (1987) 400, 123–132) was used. The affinity gel carrier was prepared as follows. 200 mg of Invention 2 was dissolved in 5 ml of 2 M phosphate buffer (pH 7.2), and 5 g of aminoagarose gel powder was suspended in the solution. 15 mg of $NaB(CN)H_3$ was added to the mixture, and the mixture was sufficiently stirred at room temperature and allowed to react for 24 hours. After the reaction was completed, the gel containing the coupling product was filtered and washed 3 times with water to be completely desalted. The desalted gel was suspended in 5 ml of 0.2 M $CH_3COONa$ solution, and 2.5 ml of acetic anhydride was added thereto, and allowed to react at 0° C. for 30 minutes and then at room temperature for 30 minutes. After the reaction was completed, the produced gel was washed to be completely desalted.

A mixture of $A_4$ aldolase, $C_4$ aldolase and hybrid-type aldolase thereof was loaded on a column packed with the gel carrier on which the glycosaminoglycan of the present invention was immobilized and equilibrated with 10 mM Tris-HCl (pH 7.5) containing 1 mM EDTA and 0.5 mM 2-mercaptoethanol. The adsorbed fraction was eluted by using a linear concentration gradient of NaCl (0 to 1.0 M) formed with two kinds of solutions: 15 ml of 10 mM Tris-HCl (pH 7.5) containing 1 mM EDTA and 0.5 mM 2-mercaptoethanol and 15 ml of 10 mM Tris-HCl (pH 7.5) containing 1.0 M NaCl, 1 mM EDTA and 0.5 mM 2-mercaptoethanol. The detection was performed by determining absorbance at 220 nm, and a NaCl concentration corresponding to the highest elution peak was measured.

Similarly, affinity chromatography was performed with carriers prepared by using, instead of Invention 2, (1) Standard HI, (2) a heparin derivative (hereafter also referred to as "2ODSH") which was obtained by treating Standard H by the method of Jaseja et al. (Can. J. Chem. (1989) 67, 1449–1456) with partial modification to remove the sulfate group bound to the hydroxyl group at the 2-position of the uronic acid residue constituting the backbone structure of Standard H through the ester bond, and (3) a heparin derivative (hereafter also referred to as "NDSH") which was obtained by treating Standard H according to the method of Inoue & Nagasawa (Carbohydr. Res. (1976) 46, 87–95) to remove the sulfate group bound to the amino group at the 2-position of the glucosamine residue constituting the backbone structure of Standard H through the ester bond and to N-acetylate the desulfated product. NaCl concentration at which the highest elution peak was obtained was measured to compare degree of affinity.

As a result, it was found that the FPA-active fraction was eluted at about 0.37 M from Standard H-immobilized gel carrier while the fraction was eluted at 0.31 to 0.33 M from gel carrier on which Invention 2, 2ODSH or NDSH was immobilized. That is, it was found that these substances have almost the same level of FPA affinity as that of Standard H.

EXAMPLE 15
[Measurement of Fructose 1,6-Bisphosphate Aldolase Inhibitory Activity of Glycosaminoglycan of the Present Invention]

The FPA inhibitory activity of the glycosaminoglycan of the present invention was measured. When the above enzyme is acted on fructose 1,6-bisphosphate (hereafter referred to as "F-1,6-P2") as a substrate, the enzyme decomposes the substrate into dihydroxyacetone phosphate (hereafter referred to as "DHAP") and glyceraldehyde 3-phosphate (GAL-3-P). When it is acted on fructose-1-phosphate (hereafter referred to as "F-1-P") as a substrate, it decomposes the substrate into DHAP and glyceraldehyde (GAL). Therefore, using F-1,6-P2 and F-1-P as substrates, the change of NADH (reduced nicoinamide adenine dinucleotide) amount was measured through measurement of change of absorbance at 340 nm, when the glycerol-3-phosphate dehydrogenase system was coupled in the presence of triose phospate isomerase and thus the produced DHAP was reduced to glycerol-3-phosphate.

Measurement was performed according to the method of Blostein & Rutter (J. Biol. Chem. (1963) 238, 3280–3285). That is, Invention 2 was added at a final concentration of 0.4 to 4 µg/ml ([I]) to 20 ml of 0.1 M glycylglycine buffer (pH 7.5) containing 50 mM F-1,6-P2 sodium salt, 0.1 M F-1-P monocyclohexylammonium salt, 4 mg of NADH and 500 µg of glycerol-3-phosphate dehydrogenase/triosephosphate isomerase complex solution. The reaction was started by the addition of 5 to 50 µl of FPA ($A_4$ aldolase ($A_4$ isoform) and $C_4$ aldolase ($C_4$ isoform) among the five kinds of isoforms of FPA, derived form bovine brain, 0.005 to 0.02 unit) to the reaction mixture. The reaction rate (v) was calculated from decrease per unit time of absorbance at 340 nm under a temperature condition of 25° C. From the results, 1/v was plotted against [I] (Dixon plot) and the Ki value of each case was calculated from the [I] intercept value.

As for the unit of FPA (activity: unit), 1 unit was defined as the amount of the enzyme cleaving 1 µmol of the substrate per minute at 25° C. in the above reaction system. The specific activity was defined as the number of units per mg of the protein.

As a negative control for the above inhibitory activity measurement, the inhibitory activity was measured by using, instead of Invention 2, 2ODSH and NDSH described in the above Example 14, chondroitin sulfate A (Seikagaku Corporation) and chondroitin sulfate C (Seikagaku Corporation).

As a result, Invention 2 exhibited FPA inhibitory activity (Table 15). In addition, it was found that the inhibition scheme of Invention 2 was competitive inhibition.

From these results, it was suggested that Invention 2 could be used as a potent FPA activity inhibitor and it may be used as pharmaceuticals such as agents for preventing infection of malaria parasites because of, for example, the action for inhibiting hypermetabolism of the glycolysis pathway.

TABLE 15

| | $A_4$ isoform (Ki value) | $C_4$ isoform (Ki value) |
|---|---|---|
| Invention 2 | 0.33 µg/ml | 2.32 µg/ml |
| 2ODSH | 0.40 µg/ml | 2.66 µg/ml |

TABLE 15-continued

|  | A$_4$ isoform (Ki value) | C$_4$ isoform (Ki value) |
|---|---|---|
| NDSH | 0.54 µg/ml | 10.80 µg/ml |
| Chondroitin sulfate A | 547.3 µg/ml | — |
| Chondroitin sulfate C | 275.8 µg/ml | — |

Note: — indicates "not measured".

EXAMPLE 16

[Example of Pharmaceutical Composition]

(1) Injection (Solution)

A lyophilized product (30 mg/ml) of Invention 2 (sodium salt) was dissolved in 5% mannitol aqueous solution at a final concentration of 5 mg/ml. The solution was subjected to sterilized filtration, and filled into ampoules in an amount of 2 ml for each ampoule to produce injection (solution).

(2) Ointment 100 mg of a lyophilized product of Invention 2 (sodium salt), 4 g of mineral oil, 8 g of petroleum jelly, 60 mg of methylparaben/propylparabene mixture, 1 g of nonionic surfactant and 30 g of purified water were uniformly mixed and filled in a container to produce an ointment.

Industrial Applicability

The present invention provides a novel glycosaminoglycan that has a structure considerably easy to be identified compared with conventional modified heparins, excellent activity for living bodies, and no anticoagulative activity and hemorrhagic activity. It also provides pharmaceuticals utilizing the activity for living bodies of the glycosaminoglycan.

What is claimed is:

1. A glycosaminoglycan having a backbone structure comprising a repetitive disaccharide bearing a uronic acid residue and a glucosamine residue, and having sulfate groups, wherein (1) a percentage of number of all glucosamine residues not having a 6-O-sulphate group relative to total glucosamine residue number in the backbone structure is not less than 95% as determined by a chemical disaccharide analysis method in which the glycosaminoglycan is decomposed with nitrous acid, reacted with para-nitrophenylhydrazine and analyzed by high performance liquid chromatography, (2) the molar % of a uronic acid residue having a sulfate group at the 2-position is not less than 45% relative to total uronic acid residues, the molar % being calculated from a disaccharide composition obtained by an enzymatic disaccharide analysis method in which the glycosaminoglycan is digested with glycosaminoglycan-degrading enzymes and analyzed by high performance liquid chromatography, and (3) an enzymatic digestivity with glycosaminoglycan-degrading enzymes is not less than 60% as determined by a method in which the glycosaminoglycan is digested by heparinase and heparitinases I and II, and analyzed by gel filtration.

2. A glycosaminoglycan having a backbone structure comprising a repetitive disaccharide bearing a uronic acid residue and a glucosamine residue, and having sulfate groups, wherein, (1) in a disaccharide composition of the glycosaminoglycan obtained by an enzymatic disaccharide analysis method in which the glycosaminoglycan is digested with glycosaminoglycan-degrading enzymes and analyzed by high performance liquid chromatography, the total of 2-acetamido-2-deoxy-4-O-(4-deoxy-α-L-threo-hex-4-enopyranosyluronic acid)-6-O-sulfo-D-glucose, 2-deoxy-2-sulfamino-4-O-(4-deoxy-α-L-threo-hex-4-enopyranosyluronic acid)-6-O-sulfo-D-glucose, 2-acetamido-2-deoxy-4-O-(4-deoxy-2-O-sulfo-α-L-threo-hex-4-O-acid)-6-O-sulfo-D-glucose and 2-deoxy-2-sulfamino-4-O-(4-deoxy-2-O-sulfo-α-L-threo-hex-4-enopyranosyluronic acid)-6-O-sulfo-D-glucose is not more than 10 mol %, and 2-deoxy-2-sulfamino-4-O-(4-deoxy-2-O-sulfo-α-L-threo-hex-4-enopyranosyluronic acid)-6-O-sulfo-D-glucose is not more than 1.5 mol %, (2) an effective disaccharide yield is not less than 60%, and (3) and enzymatic digestivity with glycosaminoglycan-degrading enzymes is not less than 60% as determined by a method in which the glycosaminoglycan is digested by heparinase and heparitinases I and II, and analyzed by gel filtration.

3. The glycosaminoglycan according to claim 2, wherein, in the disaccharide composition obtained by the enzymatic disaccharide analysis method, the total of 2-acetamido-2-deoxy-4-O-(4-deoxy-2-O-sulfo-α-L-threo-hex-4-enopyranosyluronic acid)-D-glucose, 2-deoxy-2-sulfamino-4-O-(4-deoxy-2-O-sulfo-α-L-threo-hex-4-enopyranosyluronic acid)-D-glucose, 2-acetamido-2-deoxy-4-O-(4-deoxy-2-O-sulfo-α-L-threo-hex-4-enopyranosyluronic acid)-6-O-sulfo-D-glucose and 2-deoxy-2-sulfamino-4-O-(4-deoxy-2-O-sulfo-α-L-threo-hex-4-enopyranosyluronic acid)-6-O-sulfo-D-glucose is not less than 45 mol %.

4. The glycosaminoglycan according to claim 1 or 2, wherein, in $^{13}$C-nuclear magnetic resonance spectrometry analysis of the glycosaminoglycan using a 5% solution of the glycosaminoglycan in deuterium oxide and sodium 3-(trimethylsilyl)propionate as a standard, no peak is detected at 66.5 to 67.5 ppm and signal intensities around 100 ppm and 102 ppm are higher than signal intensity around 98.3 ppm.

5. A fructose-1,6-bis-phosphate aldolase inhibitor which comprises the glycosaminoglycan as defined in claim 1 or 2 as an active ingredient.

6. A pharmaceutical composition comprising the glycosaminoglycan as defined in claim 1 or 2 as an active ingredient.

7. The pharmaceutical composition according to claim 6, which is an agent for treatment of tissue wounds and ulcers.

8. The pharmaceutical composition according to claim 6, which is-an agent for treating skin diseases.

9. The pharmaceutical composition according to claim 8, wherein the agent for treating skin diseases is an agent for promoting healing of skin wounds or an agent for treating skin ulcers.

10. A method for producing the glycosaminoglycan as defined in claim 1 or 2, which comprises the following steps of:

(a) heating a pyridine-soluble salt of glycosaminoglycan having a backbone structure comprising a repetitive disaccharide bearing a uronic acid residue and a glucosamine residue, and having sulfate groups, in pyridine at a temperature not less than 100° C. in the presence of N-methyl-N-trimethylsilyltrifluoroacetamide for a period of time that is long enough such that a percentage of number of all glucosamine residues not having a 6-O-sulphate group relative to total glucosamine residue number should be not less than 95% as determined by a chemical disaccharide arialysis method in which the glycosaminoglycan is decomposed with nitrous acid, reacted with para-nitrophenylhydrazine and analyzed by high performance liquid chromatography, (b) evaporating the pyridine from the reaction mixture obtained in the step (a), and
(c) adding water to the reaction mixture obtained in the step (b) and then placing the mixture under reduced pressure at an ordinary temperature.

* * * * *

UNITED STATES PATENT AND TRADEMARK OFFICE
CERTIFICATE OF CORRECTION

PATENT NO. : 6,492,503 B1
DATED : December 10, 2002
INVENTOR(S) : Yutaka Kariya et al.

It is certified that error appears in the above-identified patent and that said Letters Patent is hereby corrected as shown below:

Column 34,
Line 9, "sulfo-α-L-threo-hex-4-O-acid)" should be changed to -- sulfo-α-L-threo-hex-4-enopyranosyluronic acid) --

Signed and Sealed this

Fourteenth Day of October, 2003

JAMES E. ROGAN
*Director of the United States Patent and Trademark Office*